(12) United States Patent
Faraji et al.

(10) Patent No.: US 12,269,180 B2
(45) Date of Patent: Apr. 8, 2025

(54) STEREOSCOPIC VISUALIZATION CAMERA AND INTEGRATED ROBOTICS PLATFORM WITH FORCE/TORQUE SENSOR NON-LINEARITY CORRECTION

(71) Applicant: Digital Surgery Systems, Inc., Goleta, CA (US)

(72) Inventors: Hossein Faraji, Goleta, CA (US); Stephen Minne, Goleta, CA (US); Michael Larkin, Goleta, CA (US)

(73) Assignee: Digital Surgery Systems, Inc., Goleta, CA (US)

( * ) Notice: Subject to any disclaimer, the term of this patent is extended or adjusted under 35 U.S.C. 154(b) by 277 days.

(21) Appl. No.: 17/951,536

(22) Filed: Sep. 23, 2022

(65) Prior Publication Data

US 2023/0110248 A1 Apr. 13, 2023

Related U.S. Application Data

(60) Provisional application No. 63/248,297, filed on Sep. 24, 2021.

(51) Int. Cl.
*B25J 9/16* (2006.01)
*A61B 90/00* (2016.01)
*A61B 90/25* (2016.01)

(52) U.S. Cl.
CPC .......... *B25J 9/1697* (2013.01); *B25J 9/1692* (2013.01); *A61B 90/25* (2016.02); *A61B 90/37* (2016.02)

(58) Field of Classification Search
CPC ....... B25J 9/1697; B25J 9/1692; A61B 90/25; A61B 90/37; A61B 90/361; A61B 2090/064; A61B 2090/066; A61B 34/30
See application file for complete search history.

(56) References Cited

U.S. PATENT DOCUMENTS

| 8,375,808 B2 * | 2/2013 | Blumenkranz ...... B25J 15/0009 73/862.044 |
| 2020/0238526 A1 * | 7/2020 | Nammoto ................ B25J 9/163 |
| 2023/0054209 A1 * | 2/2023 | Roh ....................... G16H 20/40 |

* cited by examiner

*Primary Examiner* — Ian Jen
*Assistant Examiner* — Renee LaRose
(74) *Attorney, Agent, or Firm* — K&L Gates LLP; Dennis A. Majewski

(57) ABSTRACT

New and innovative systems and methods for calibrating and correcting sensors associated with a collaborative robot are disclosed. An example system comprises: at least one robotic arm; a sensor affixed to a location on the robotic arm, wherein the sensor measures force and torque across six degrees of freedom (6DOF); a processor; and memory. The system may receive, from the sensor, sensor input in real-time that indicate a measured force or torque. The system may generate, in real-time, sensor corrections that correspond to offset, linear, and non-linear deviations of the measured force in each sensor axis. The sensor corrections may correspond to offset, linear, and non-linear cross-coupling of the measured force between two or more sensor axes. The sensor corrections may be determined by applying offset, linear, and non nonlinear corrections to each degree of freedom (DOF) from every other DOF.

20 Claims, 26 Drawing Sheets

1502A
1502B 1504A
1504B 1506A
1506B

|  | Average (abs) Error Forces (N) | Average (abs) Error Forces (N) After correction | Average (abs) Error Torques (N.m) | Average (abs) Error Torques (N.m) After correction |
| --- | --- | --- | --- | --- |
| Dataset 1 | 2.682 | 1.572 | 0.309 | 0.135 |
| Dataset 2 | 2.466 | 1.576 | 0.311 | 0.196 |

FIG. 25

STEREOSCOPIC VISUALIZATION CAMERA AND INTEGRATED ROBOTICS PLATFORM WITH FORCE/TORQUE SENSOR NON-LINEARITY CORRECTION

PRIORITY CLAIM

The present application claims priority to and the benefit of U.S. Provisional Patent Application 63/248,297, filed Sep. 24, 2021, the entirety of which is incorporated herein by reference.

TECHNICAL FIELD

Certain aspects of the present disclosure generally relate to surgical systems, and specifically relate to systems and methods for a stereoscopic visualization camera and integrated robotics platform.

BACKGROUND

Currently known surgical stereoscopic cameras are connected to robotic arms to help provide maneuverability. Since the camera and robotic arm can be heavy, many robotic arms have joints that are controlled by motors. Typically a force/torque sensor is located at an end-effector of the robotic arm at or adjacent to a connection point with the stereoscopic camera. The force/torque sensor is configured to sense how an operator moves, pulls, or otherwise attempts to manipulate the stereoscopic camera as part of a collaborative robot application. Data from the force/torque sensor is processed to determine which joints of the robotic arm are moved (and at what speed) to achieve the desired movement of the operator. The end result is a motor-assisted robotic arm that moves effortlessly when pushed, pulled, or otherwise manipulated by an operator.

The force/torque sensor typically has non-linearity characteristics, especially when the end-effector of the robotic arm is connected to a relatively heavy stereoscopic camera. This non-linearity can affect control of the robotic arm over some orientations and/or operator-induced motions. This is a particular problem in sensitive applications such as robotic control in medical devices.

Known solutions for compensating for sensor non-linearity may include frequent re-zeroing of the sensor and applying advanced computational techniques such as a neural network. However, both of these solutions have known problems. For instance, re-zeroing of the sensor cannot occur in real-time, and is not effective if a majority of the force is translated from one axis to another. Additionally, neural networks can be effective but require extensive computational resources and amount of data that renders this solution impractical in most common situations.

A need accordingly exists for sensor non-linearity correction in collaborative robot applications.

SUMMARY

The present disclosure provides new and innovative systems and methods for calibrating and correcting sensors associated with a collaborative robot.

In an example, a system comprises at least one robotic arm, a sensor affixed to a location on the robotic arm, wherein the sensor measures force and torque across six degrees of freedom (6DOF), a processor, and a memory is disclosed. The memory stores computer-executable instructions that, when executed by the processor, cause the system to perform one or more steps. For example, the system may receive, from the sensor, sensor input in real-time. The sensor input may indicate a measured force applied at the location of the sensor in real-time. The system may generate, in real-time, sensor corrections to the sensor input. The sensor corrections may correspond to offset, linear, and non-linear deviations of the measured force in each sensor axis. The sensor corrections may correspond to offset, linear, and non-linear cross-coupling of the measured force between two or more sensor axes. Furthermore, the sensor corrections may be based on a generalized method of applying offset, linear, and non nonlinear corrections to each degree of freedom from every other degree of freedom.

In another example, a system comprising at least one robotic arm, a sensor affixed to a location on the robotic arm, wherein the sensor measures force and torque across six degrees of freedom (6DOF), a processor, and memory is disclosed. The memory stores computer-executable instructions that, when executed by the processor, causes the system to perform one or more steps. For example, the system may determine, when the at least one robotic arm is not in use, a baseline value for the sensor; and may generate, based on the baseline value of the sensor, a correction model based on the baseline value of the sensor. The system may receive, in real-time when the at least one robotic arm is in use, a sensor input from the sensor indicating a measured force. The system may generate, based on training data associated with the sensor, correction parameters for the correction model. The system may apply, in real-time, the correction model to the sensor input to generate a sensor correction for the sensor input.

In an example, a method performed by a computing device having one or more processors may include: determining, when the robotic arm is not in use, a baseline value for the sensor; generating, based on the baseline value of the sensor, a correction model based on the baseline value of the sensor; receiving, in real-time when the at least one robotic arm is in use, a sensor input from the sensor indicating a measured force; generating, based on training data associated with the sensor, correction parameters for the correction model; and applying, in real-time, the correction model to the sensor input to generate a sensor correction for the sensor input.

In an example, a non-transitory computer-readable medium for use on a computer system is disclosed. The non-transitory computer-readable medium may contain computer-executable programming instructions may cause processors to perform one or more steps or methods described herein.

BRIEF DESCRIPTION OF THE FIGURES

FIG. 25 is a table showing error correction of measured forces and torques in two training datasets.

DETAILED DESCRIPTION

The present disclosure relates in general to force and/or torque sensors ("force/torque sensor(s)") of robotic arm(s) used in surgical sites. An example of a force/torque sensor may comprise a six degrees of freedom (6-DOF) device capable of measuring a plurality of forces and torques applied to and/or perceived by the sensor. The force/torque sensor may be mounted on a component of a robotic arm (e.g., an end-effector of a manipulator) to equip the robotic arm with force/torque sensing capabilities. The force/torque sensor typically needs to be calibrated so that accurate data is presented from raw sensor data. Most commercial force/torque sensors have non-linearity characteristics, e.g., where errors in force or torque measurements increase non-linearly leading to more difficulties in calibration. The uncertainty in proper calibration is particularly problematic for the application of force/torque sensors in delicate environments such as surgical sites and/or where acute robotic control is involved. As previously discussed, known solutions for compensating for sensor non-linearity include frequent re-zeroing of the sensor and applying advanced computational techniques such as a neural network. However, both of these solutions have known problems. For instance, re-zeroing of the sensor cannot occur in real-time, and is not effective if a majority of the force is translated from one axis to another. Additionally, neural networks can be effective but require extensive computational resources and amount of data that renders this solution impractical in most common situations.

Various embodiments of the present disclosure address one or more of the above described shortcomings. For example, systems and methods presented herein involve multiple dimensions of non-linearity and cross-coupling of the robotic arm through a simple and quick calibration, resulting in performance improvements that allow high performance applications to be accomplished. Such systems and methods can be applicable to a variety of force-torque sensors and may require minimal computing resources. Furthermore, such systems and methods for calibration can work in real-time and be particularly suited for a surgical environment.

I. Exemplary Surgical Environment for the Force/Torque Sensor

Figure 1:
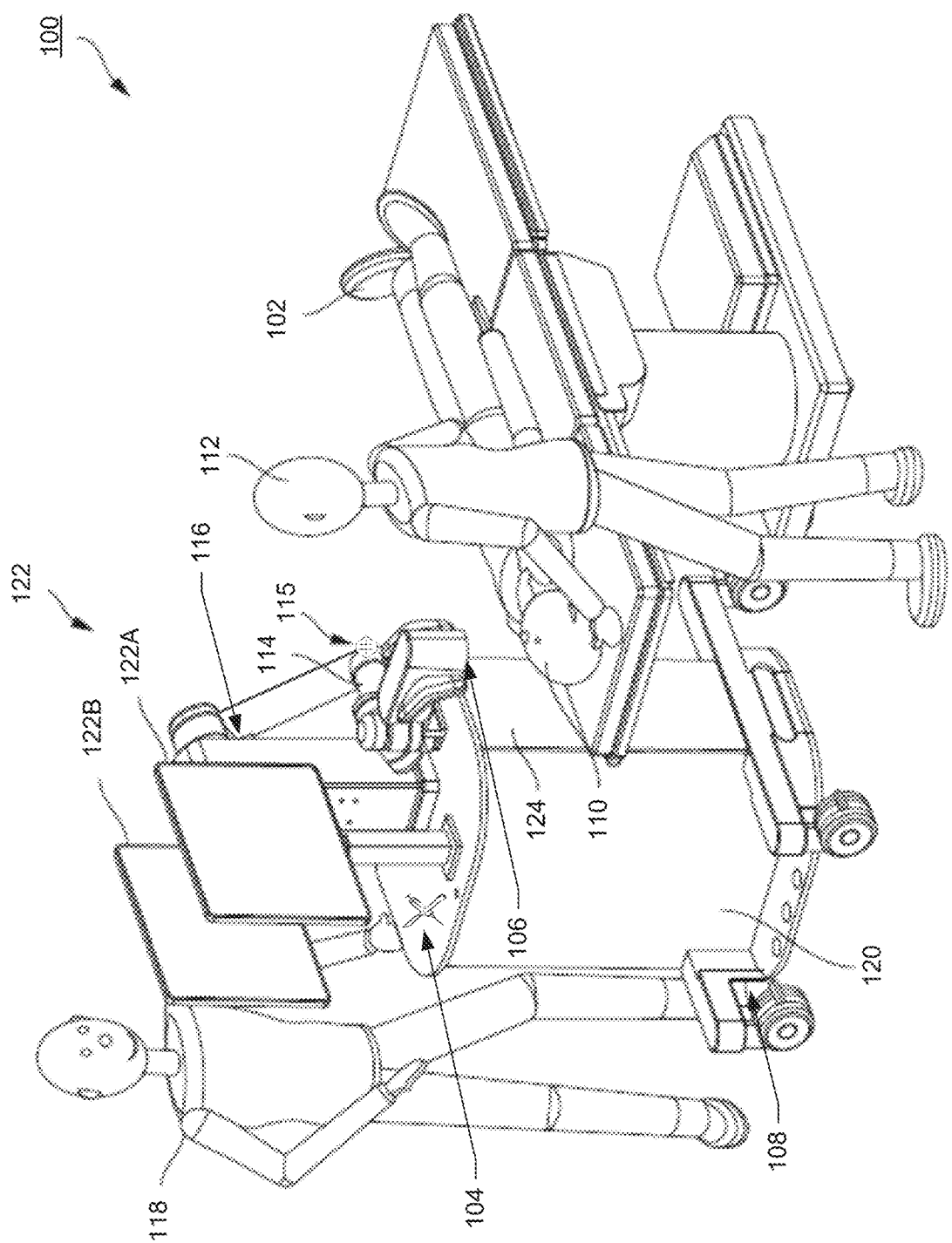
FIGS. 1 and 2 show diagrams of a surgical environment including one or more robotic arms having a force/torque sensor, according to example embodiments of the present disclosure.
Figure 2:
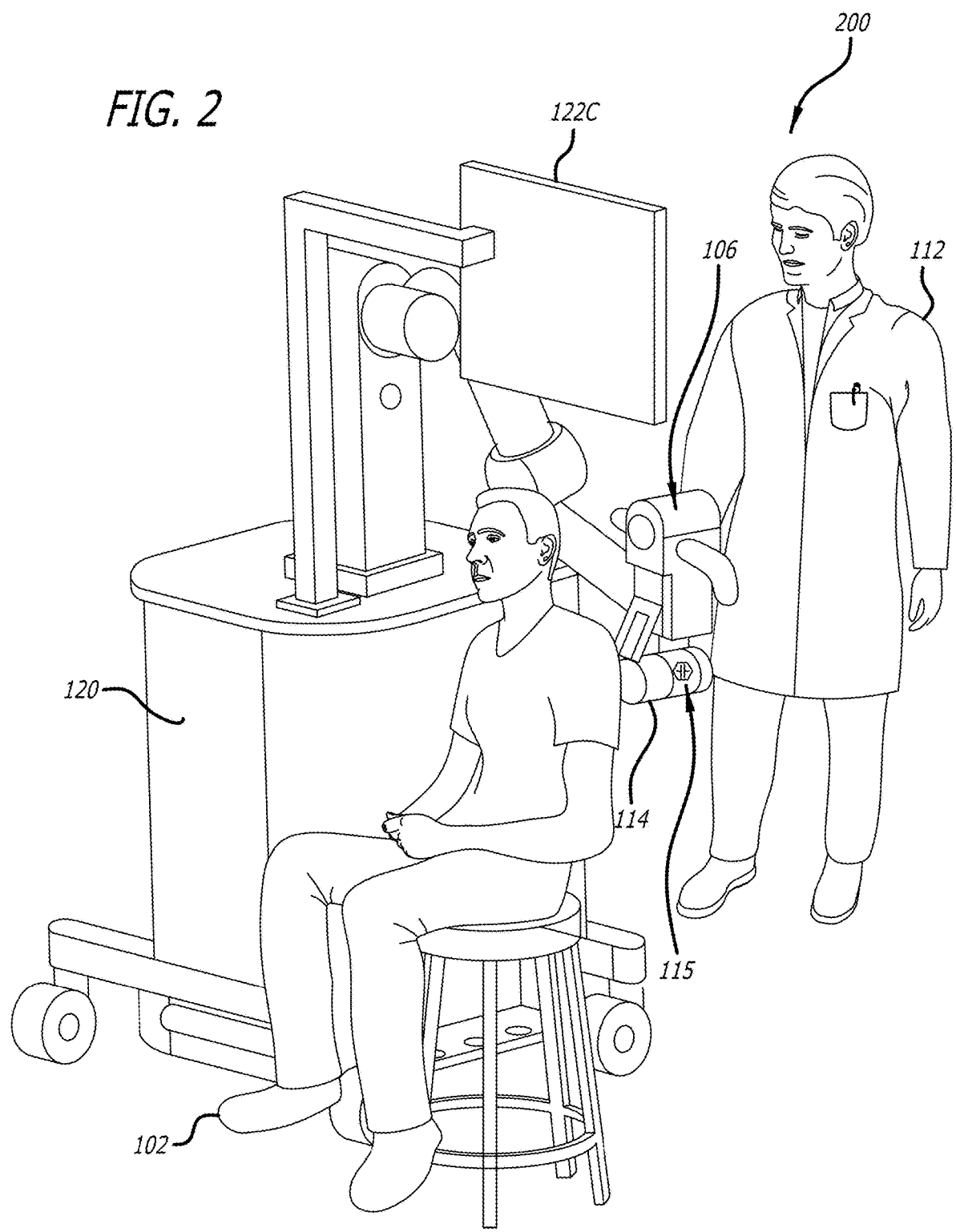

FIGS. 1 and 2 show diagrams of a surgical environment including one or more robotic arms having a force/torque sensor, according to example embodiments of the present disclosure. The surgical environment may include a patient 102 that is subjected to or intended to be subjected to a surgical procedure, surgical tools 104, surgical camera (e.g., a stereoscopic visualization camera 106), robotic controls (e.g., a foot pedals 108), at least one robotic arm 114, a surgeon 112, and a surgeon assistant 118. In at least one embodiment, the surgical camera may comprise a stereoscopic visualization camera 106 used within a microsurgical environment 100, according to example embodiments of the present disclosure. The small footprint and maneuverability of the stereoscopic visualization camera (especially when used in conjunction with a multiple-degree of freedom arm) enables flexible positioning with respect to a patient 102. A portion of the patient 102 in view of the stereoscopic visualization camera 106 includes a target site 110. A surgeon 112 can position the stereoscopic visualization camera 106 in virtually any orientation while leaving more than sufficient surgical space above the patient 102 (lying in the supine position). The stereoscopic visualization camera 106 accordingly is minimally intrusive (or not intrusive) to enable the surgeon 112 to perform a life-altering microsurgical procedure without distraction or hindrance.

In FIG. 1, the stereoscopic visualization camera 106 is connected to a mechanical arm 114 via mounting bracket 116. The robotic arm 114 may include one or more rotational or extendable joints with electromechanical brakes to facilitate easy repositioning of the stereoscopic visualization camera 106. Furthermore, at least one region of the robotic arm may be equipped with or affixed to a force/torque sensor 115. As will be discussed further herein, the force/torque sensor may comprise a 6-DOF device capable of measuring a plurality of forces and torques applied to and/or perceived at the location of the robotic arm.

In one embodiment, in order to move the stereoscopic visualization camera 106, the surgeon 112, or the assistant 118, may actuate brake releases (e.g., as part of robotic controls 108) on one or more joints of the robotic arm 114. After the stereoscopic visualization camera 106 is moved into a desired position, the brakes may be engaged to lock the joints of the robotic arm 114 in place.

In some aspects, the stereoscopic visualization camera 106 may not necessarily include oculars. The absence of oculars may mean that the stereoscopic visualization camera 106 need not have to be aligned with the eyes of the surgeon 112. This freedom may allow the stereoscopic visualization camera 106 to be positioned and orientated in desirable positions that may not have been practical or possible with prior known surgical microscopes. In other words, the surgeon 112 can perform microsurgery with the most optimal view for conducting the procedure rather than being restricted to merely adequate view dictated by oculars of a surgical microscope.

Returning to FIG. 1, the stereoscopic visualization camera 106, via the mechanical arm 114, is connected to a cart 120 with display monitors 122A and 122B (collectively a stereoscopic visualization platform 122). In the illustrated configuration, the stereoscopic visualization platform 122 is self-contained and may be moved to any desired location in the microsurgical environment 100 including between surgical rooms. The integrated stereoscopic visualization platform 122 enables the stereoscopic visualization camera 106 to be moved and used on-demand without time needed to configure the system by connecting the display monitors 122A and 122B.

The display monitors 122A and 122B may include any type of display including a high-definition television, an ultra-high definition television, smart-eyewear, projectors, one or more computer screens, laptop computers, tablet computers, and/or smartphones. The display monitors 122A and 122B may be connected to mechanical arms to enable flexible positioning similar to the stereoscopic visualization camera 106. In some instances, the display monitors 122A and 122B may include a touchscreen to enable an operator to send commands to the stereoscopic visualization camera 106 and/or adjust a setting of a display.

In some embodiments, the cart 120 may include a computer 124. In these embodiments, the computer 124 may control a robotic mechanical arm connected to the stereoscopic visualization camera 106. Additionally or alternatively, the computer 124 may process raw sensor data received from force/torque sensor 115 of the robotic arm 114. As will be described further, the computer 124 may perform calibration of the force/torque sensor across multiple dimensions in real-time to resolve any non-linearity in received sensor data, in order to provide accurate force/torque measurements in real-time. The computer 124 may also be used to store raw sensor data received over time into a file (stored to a memory). Such data may be used as training data for the force/torque sensor to learn correct calibration parameters. Further, the computer 124 may also send control signals to the stereoscopic visualization camera 106 to select settings and/or perform calibration.

In some aspects, the computer 124 may process video (or stereoscopic video) signals (e.g., an image or frame stream) from the stereoscopic visualization camera 106 for display on the display monitors 122A and 122B.

FIG. 2 shows a diagram of the microsurgical environment 100 with the patient 102 in a sitting position for a posterior-approach skull base neurosurgery. In the illustrated embodiment, the stereoscopic visualization camera 106 is placed into a horizontal position to face the back of the head of the patient 102. The mechanical robotic arm 114 includes joints that enable the stereoscopic visualization camera 106 to be positioned as shown. In addition, the cart 120 includes a monitor 122C, which may be aligned with the surgeon's natural view direction.

The absence of oculars enables the stereoscopic visualization camera 106 to be positioned horizontally and lower than the eye-level view of the surgeon 112. Further, the relatively low weight and flexibility enables the stereoscopic visualization camera 106 to be positioned in ways unimaginable for other known surgical microscopes. The stereoscopic visualization camera 106 thereby provides a microsurgical view for any desired position and/or orientation of the patient 102 and/or the surgeon 112. Like in FIG. 1, the robotic arm 114 leading to the stereoscopic visualization camera 106 may be equipped with a force/torque sensor 115 to measure the force and/or torque applied to and/or perceived at the location of the force/torque sensor 115.

While FIGS. 1 and 2 show two example embodiments for positioning the stereoscopic visualization camera 106, it should be appreciated that the stereoscopic visualization camera 106 may be positioned in any number of positions depending on the number of degrees of freedom of the mechanical robotic arm 114. It is entirely possible in some embodiments to position the stereoscopic visualization camera 106 to face upwards (e.g., upside down).

II. Example Robotics System for the Stereoscopic Visualization Camera

As discussed in connection with FIGS. 1 and 2, an example stereoscopic visualization camera 106 may be connected to a mechanical or robotic arm 114 as part of a stereoscopic visualization platform or stereoscopic robotic platform. The example robotic arm 114 is configured to enable an operator to position and/or orient the stereoscopic visualization camera 106 above and/or next to a patient during one or more procedures. Accordingly, the robotic arm 114 enables an operator to move the stereoscopic visualization camera 106 to a desired field-of-view ("FOV") of a target surgical site. Surgeons generally prefer cameras to be positioned and/or orientated in a FOV that is similar to their own FOV to enable easier visual orientation and correspondence between images displayed on a screen and the surgeon's FOV. The example robotic arm 114 disclosed herein provides structural flexibility and assisted control to enable positioning to coincide or to be consistent with a surgeon's FOV without blocking the surgeon's own FOV.

Figure 3:
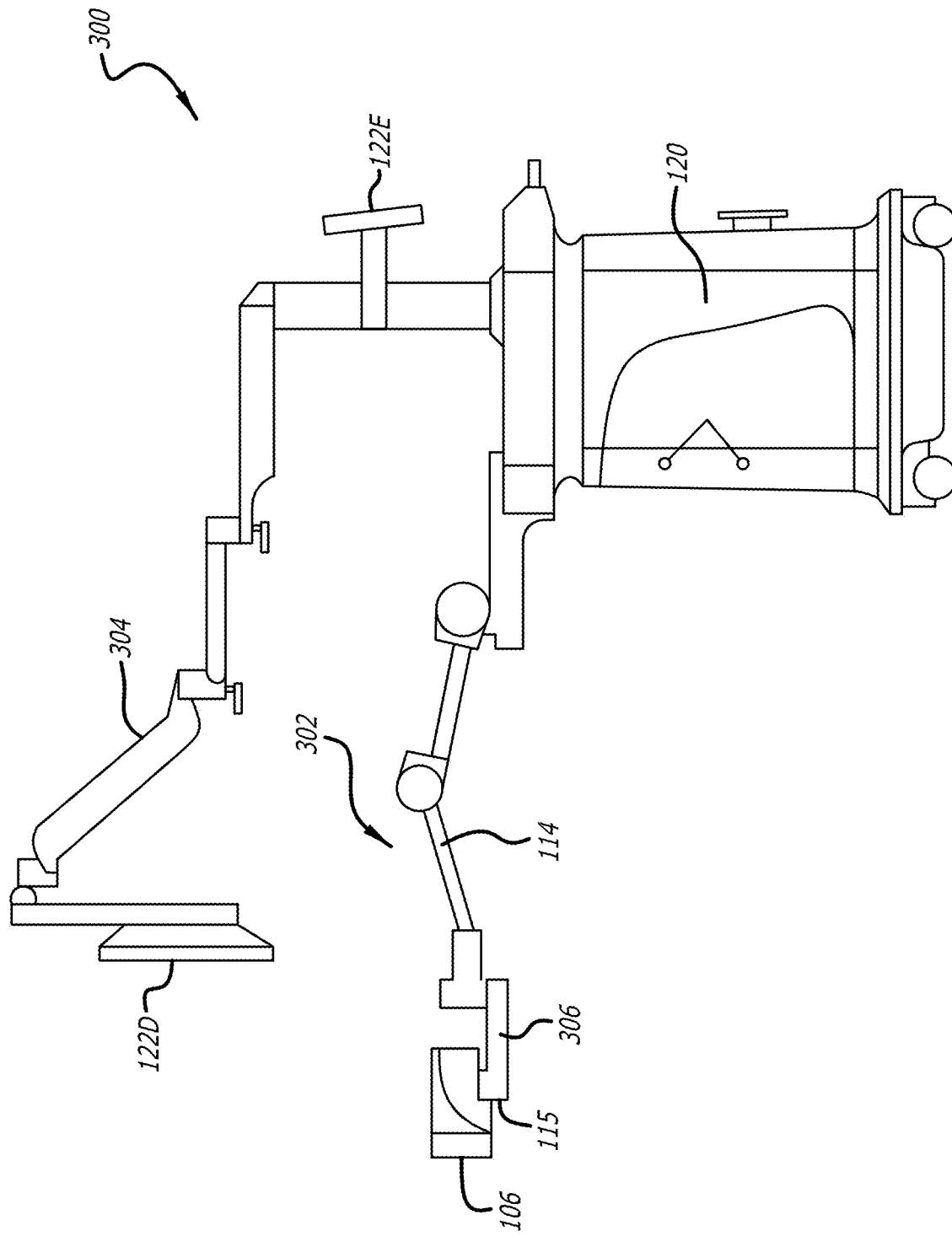
FIG. 3 shows a side-view of the microsurgical environment of FIGS. 1 and 2, according to an example embodiment of the present disclosure.
Figure 4:
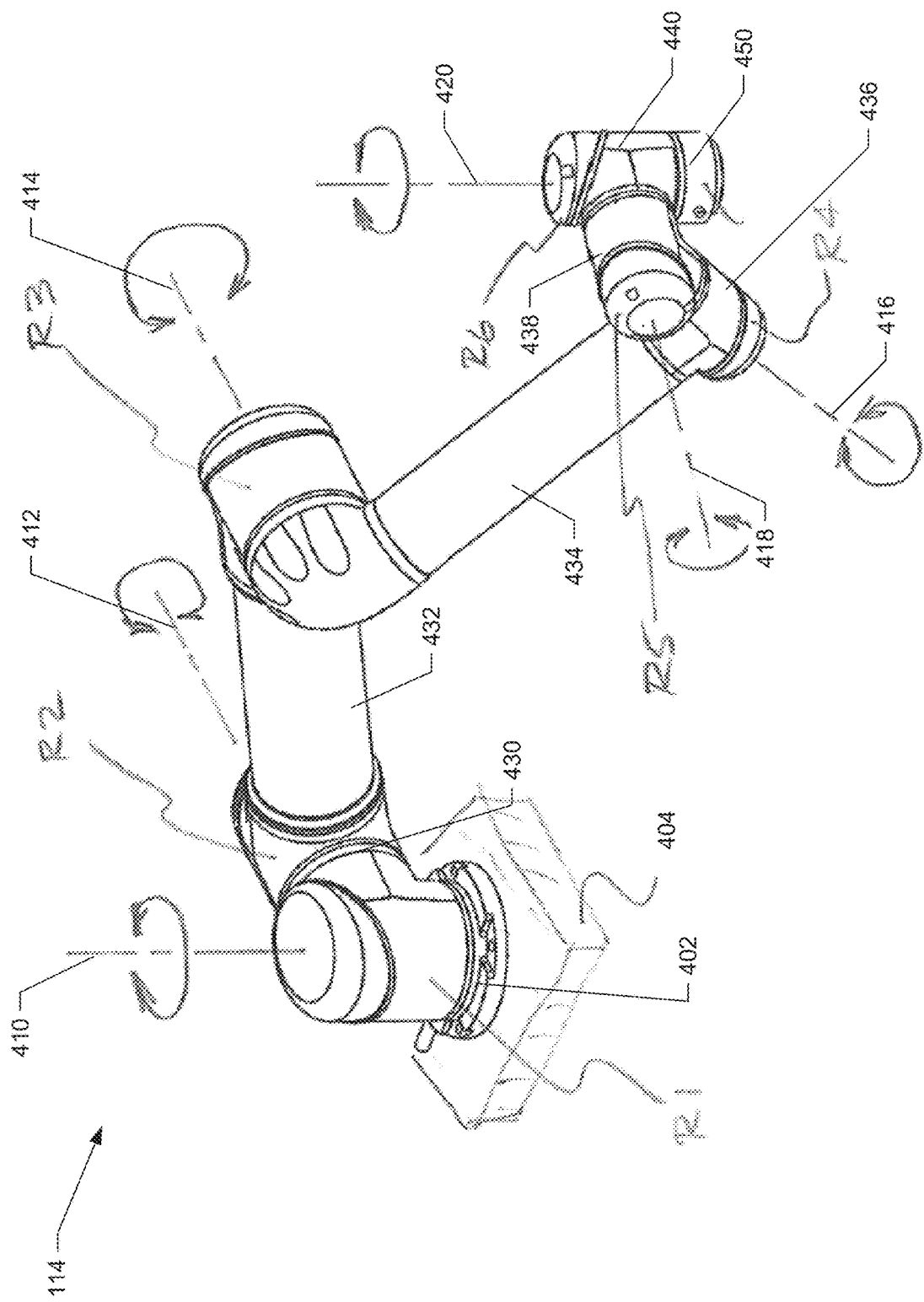
FIG. 4 shows an embodiment of an example robotic arm having a force/torque sensor, according to an example embodiment of the present disclosure.

FIGS. 3 and 4 illustrate an example of a stereoscopic robotic platform, in accordance with a non-limiting embodiment of the present disclosure. The example stereoscopic robotic platform 302 disclosed herein includes the example stereoscopic visualization camera 106 connected to the robotic arm 114, as previously described in relation to FIGS. 1 and 2. Stereoscopic images recorded by the camera 106 may be displayed via one or more display monitors 122D and 122E, similar to monitors 122A-C previously described in relation to FIGS. 1 and 2. The robotic arm 114 is mechanically connected to the cart 120 (described previously in relation to FIGS. 1 and 2), which may also support one or more of the display monitors 122D, 122E. The robotic arm may include, for example, an articulated robotic arm generally anthropomorphic in size, nature, function, and operation.

Specifically, FIG. 3 shows a side-view of the microsurgical environment 300, according to an example embodiment of the present disclosure. In the illustrated example, the display monitor 122D may be connected to the cart 120 via a mechanical arm 304 with one or more joints to enable flexible positioning. In some embodiments, the mechanical arm 304 may be long enough to extend over a patient during surgery to provide relatively close viewing of a surgeon.

Moreover, FIG. 3 also illustrates a side-view of the stereoscopic robotic platform 302, including the stereoscopic visualization camera 106 and the robotic arm 114. The camera 106 is mechanically coupled to the robotic arm 114 via a coupling plate 306. In some embodiments, the coupling plate 306 may include one or more joints that provide for further degrees of positioning and/or orientation of the camera 106. In some embodiments, the coupling plate 306 has to be manually moved or rotated by an operator. For example, the coupling plate 306 may have a joint that enables the camera 106 to be positioned quickly between having an optical axis along a z-axis (i.e., pointing downward toward a patient) and an optical axis along an x-axis or y-axis (i.e., pointing sideward toward a patient).

The example coupling plate 306 may include a sensor 115 configured to detect forces and/or torques imparted by an operator for moving the camera 106, as previously described in relation to FIGS. 1 and 2 (e.g., force/torque sensor 115 in FIGS. 1 and 2). The user may position and/or orient the camera 106 with assistance from the robotic arm 114. The sensor 115 detects a force vector or torque angle provided by the operator. The example platform 302 disclosed herein uses the sensed force/torque to determine which joints of the robotic arm 114 should be rotated (and how quickly the joints should be rotated) to provide assisted movement of the camera 106 that corresponds to the forces/torques provided by the operator. The sensor 115 may be located at an interface between the coupling plate 306 and the camera 106 for detecting the forces and/or torques imparted by an operator via the mechanical arms 304.

In some embodiments, the sensor 115 may include, for example, a six-degrees-of-freedom haptic force-sensing module. In these embodiments, the sensor 115 may detect translational force or motion in the x-axis, y-axis, and z-axis. The sensor 115 may also separately detect rotational force or motion around a yaw-axis, a pitch-axis, and a roll-axis. The decoupling of the translational force and the rotational force may enable the stereoscopic robotic platform 302 to more easily calculate direct and/or reverse kinematics for control of the robot arm 114.

The example sensor 115 may be configured to detect force since the robotic arm 114 may not be movable by a user alone. Instead, the sensor 115 detects translational and rotational force applied by a user, which is used by the stereoscopic robotic platform 302 to determine which joints to rotate to provide assisted movement control of the robotic arm 114. In other examples, the robotic arm 114 may permit operator movement without assistance, or at least initial assistance. In these other examples, the sensor 115 detects motion imparted by the user, which is used by the stereoscopic robotic platform 302 to subsequently cause one or more joints to rotate, thereby providing assisted movement. The time between initial detection of motion or the force resulting in the motion, until the stereoscopic robotic platform 302 causes the joints to rotate may be less than 200 milliseconds ("ms"), 100 ms, 50 ms, or as few as 10 ms, where the user does not notice the initial time of unassisted movement of the robotic arm 114.

The example sensor 115 may output digital data that is indicative of the rotational force/motion and digital data that is indicative of the translational force/motion. In this example, the digital data may have 8, 16, 32, or 64 bit resolution for the detected force/motion in each axis. Alternatively, the sensor 115 may transmit an analog signal that is proportional to the sensed force and/or motion. The example sensor 115 may transmit the data at a periodic sampling rate of, for example, 1 ms, 5 ms, 10 ms, 20 ms, 50 ms, 100, ms, etc. Alternatively, the sensor 115 may provide a near-continuous stream of force/motion data.

In some embodiments, the example sensor 115 may instead be located in one or more of control arms between the control arms associated with the camera 106, as will be described in relation to FIG. 11. In examples, where each of the control arms includes a sensor 115, the example stereoscopic robotic platform 302 may receive two sets of translational and rotational force or motion. In these examples, the stereoscopic robotic platform 302 may average the values from the sensors 115.

As will be described further, systems and methods are disclosed for calibrating the force/torque sensor 115 across multiple dimensions in real-time to resolve any non-linearity in received sensor data. The real-time calibration will assist in providing accurate force/torque measurements in real-time.

In the illustrated embodiments, a first end of the robotic arm 114 may be mounted to the cart 120 while a second, opposite end of the robotic arm is mechanically connected to stereoscopic visualization camera 106 (e.g., a robot end effector). FIG. 3 shows the robotic arm 114 holding the stereoscopic visualization camera 106 in an extended position, such as positioning the stereoscopic visualization camera 106 above a surgical site while keeping the rest of the platform 302 out of the way of a surgeon. The cart 120 can be configured to securely hold the stereoscopic robotic platform 302 and can be weighted and balanced to prevent tipping under prescribed operating positions.

A. Robotic Arm Embodiment

FIG. 4 illustrates an embodiment of the example robotic arm 114, according to an example embodiment of the present disclosure. In some embodiments, the robotic arm 114 is similar to or comprises model UR5 from Universal Robots S/A. The exterior surfaces of the robotic arm 114 comprise aluminum and plastic materials, which are compatible for use in an operating room and easily cleaned.

While the robotic arm 114 is described herein as being electromechanical, in other examples, the robotic arm 114 may be mechanical, hydraulic, or pneumatic. In some embodiments, the robotic arm 114 may have mixed actuation mechanisms, for example, using a vacuum chuck with a control valve to hold and manipulate the camera 106. Further, while the robotic arm 114 is described below as including a certain number of joints and links, it should be appreciated that the robotic arm 114 may include any number of joints, any lengths of links, and/or comprise any types of joints, or sensors.

As described herein, the robotic arm 114 is situated and the joints are oriented to provide an unrestricted view of an operating field while providing a 3D stereoscopic display for an operator for any surgical procedure for a patient. Movement of the robotic arm 114 in noncritical motions is provided to be fast enough for an operator to be convenient yet safe. Movement of the robotic arm 114 is controlled during surgery to be meticulous and accurate. In addition, movement of the robotic arm is controlled to be smooth and predictable through the entire range of motion required for a surgical procedure. As described herein, movement of the robotic arm 114 is controllable by remote control or via manual manipulation of the arm itself. In some embodiments, the robotic arm 114 is configured to be positionable with minimal force (e.g., via an assisted guidance feature) with just the use of, for example, a single auricular finger.

In some embodiments, the robotic arm 114 may include mechanically or electronically locking brakes on the joints. The brakes may be engaged once the aim or "pose", which is generally the location and direction, of the camera 106 after it is set by an operator. The robotic arm 114 may include a locking or unlocking switch or other input device to prevent undesired manual or accidental motion. When locked, the example robotic arm provides sufficient stability that enables the stereoscopic visualization camera 106 to provide a stable, clear image. The robotic arm 114 may additionally or alternatively include one or more dampening devices to absorb or attenuate vibrations following movement of the stereoscopic visualization camera 106 to a new pose. The dampening devices may include, for example, fluid-filled linear or rotational dampeners, rubber-based vibration isolation mounting dampeners, and/or tuned mass-spring dampeners. Alternatively, or in addition, the arm 114 may include electromechanical dampening, for example, through the use of a proportional integral derivative ("PID") servo system.

The example robotic arm 114 may be configured with a stowage position to which one or more links are returned for transportation and storage. A stowage position enables the robotic arm to be transported and stored in a concise footprint yet deployed with a long reach required in some surgical procedures. Cables, such as those routed for the stereoscopic visualization camera 106, are provided along the robotic arm 114 so as to avoid interference with a surgical procedure.

In the illustrated embodiment of FIG. 4, the robotic arm 114 includes six joints, labeled R1, R2, R3, R4, R5, and R6. In other embodiments, the robotic arm 114 may include fewer or additional joints. Additionally, in some embodiments, at least some of the joints R1 to R6 have rotational motion capabilities of +/−360°. The rotational motion may be provided by an electromechanical subsystem that includes, for each joint, an electric motor configured to drive a mechanical rotational joint through one or more anti-backlash joint gearboxes. Each of the joints R1 to R6 may include one or more rotational sensors to detect joint position. Further, each joint may include a slip clutch and/or an electromechanical brake.

Each of the joints R1 to R6 may have an overall repeatability of motion (with the camera 106 attached) of approximately +/−1/10 of a millimeter ("mm"). The joints may be have variable rotational speeds that can be controlled between 0.5° to 180° per second. Together, this translates to camera movement between 1 mm per second to 1 meter per second. In some embodiments, the stereoscopic robotic platform 302 may have speed governors for one or more of the joints R1 to R6 that are in place during surgical procedures. Each of the joints R1 to R6 may be electrically connected to a power source and/or command line in a controller of the robotic arm 114. Wires for power and command signals may be routed internally within the joints and links. Further, one or more of the joints may include dampeners, such as o-rings for connection to links. The dampeners may, for example, reduce or absorb vibrations in the robotic arm 114, vibrations from the cart 120, and/or vibrations imparted via the stereoscopic visualization camera 106.

Joint R1 includes a base joint that is mechanically coupled to a flange 402, which is secured to a stationary structure 404. The flange 402 may include any type of mechanical connector. The stationary structure 404 may include, for example, the cart 120 of FIG. 3, a wall, a ceiling, a table, etc. The joint R1 is configured to rotate around a first axis 410, which may include the z-axis.

Joint R1 is connected to joint R2 via a link 430. The example link 430 includes a cylinder or other tubular structure configured to provide structural support for the downstream sections of the robotic arm 114. The link 430 is configured to provide a rotational secure connection with joint R2 to enable joint R2 to rotate while the link 430 is held in place by its connection to the joint R1. Joint R2 may include, for example, a shoulder joint configured to rotate around an axis 412. The example axis 412 is configured to be perpendicular (or substantially perpendicular) to axis 410. The axis 412 is configured to be within an x-y plane given the rotation of the joint R1 around the z-axis.

Joint R2 is mechanically coupled to joint R3 via link 432. The link 432 is configured to have a greater length than the link 430 and is configured to provide structural support for downstream portions of the robotic arm 114. Joint R3 may include, for example, an elbow joint. Together with joint R2, joint R3 provides extensible positioning and/or orientating of the robotic arm 114. The joint R3 is configured to rotate around an axis 414, which is perpendicular or orthogonal to the axis 410 and parallel to the axis 412.

Joint R3 is connected to joint R4 via link 434, which provides structural support for downstream portions of the robotic arm 114. The example joint R4 may be, for example, a first wrist joint configured to provide rotation around axis 416, which may be orthogonal to the axes 412 and 414. Joint R4 is mechanically connected to joint R5 via link 436. Joint R5 may be a second wrist joint configured to provide rotation around an axis 418, which is orthogonal to axis 416. Joint R5 is mechanically connected to joint R6 via link 438. Joint R6 may be a third wrist joint configured to rotate around axis 420, which is orthogonal to the axis 418. Together, the wrist joints R4 to R6 provide precise flexibility in positioning the stereoscopic visualization camera 106 described herein.

The example robotic arm 114 includes a connector 450. The example connector 3450 is connected to joint R6 via link 440. In some embodiments, the example link 440 may include a sleeve that enables joint R6 to rotate the connector 450. As discussed herein, the connector 3450 may be configured to mechanically couple to the coupling plate 306 or the stereoscopic visualization camera 106 directly when a coupling plate is not used. The connector 450 may include one or more screws to secure the robotic arm 114 to the coupling plate 304 and/or the stereoscopic visualization camera 106.

In some embodiments, the robotic arm 114 of the illustrated example may have a maximum reach of 85 mm, in an orientation roughly similar to a human arm. The arm 114 may have a payload capacity of 5 kilograms. Further, the arm 114 may be configured as a "collaborative" device to enable safe operation in the proximity of humans. For example, the maximum force that the robotic arm 114 can apply to external surfaces is controlled. Should a portion of the robot arm unexpectedly contact another object, the collision is detected, and motion is instantly ceased. During an emergency stop situation where for example, power is lost the joints R1 to R6 can be back-driven or manually rotated such that an operator can grab part of the robotic system and swing it out of the way. For example, slip clutches within the joints limit the maximum torque the joint motor can apply rotationally to the arm 114 during operation. When powered off, the slip clutches of the joints slip when manually manipulated to allow an operator to quickly move the robotic arm 114 out of the way.

Figure 5:
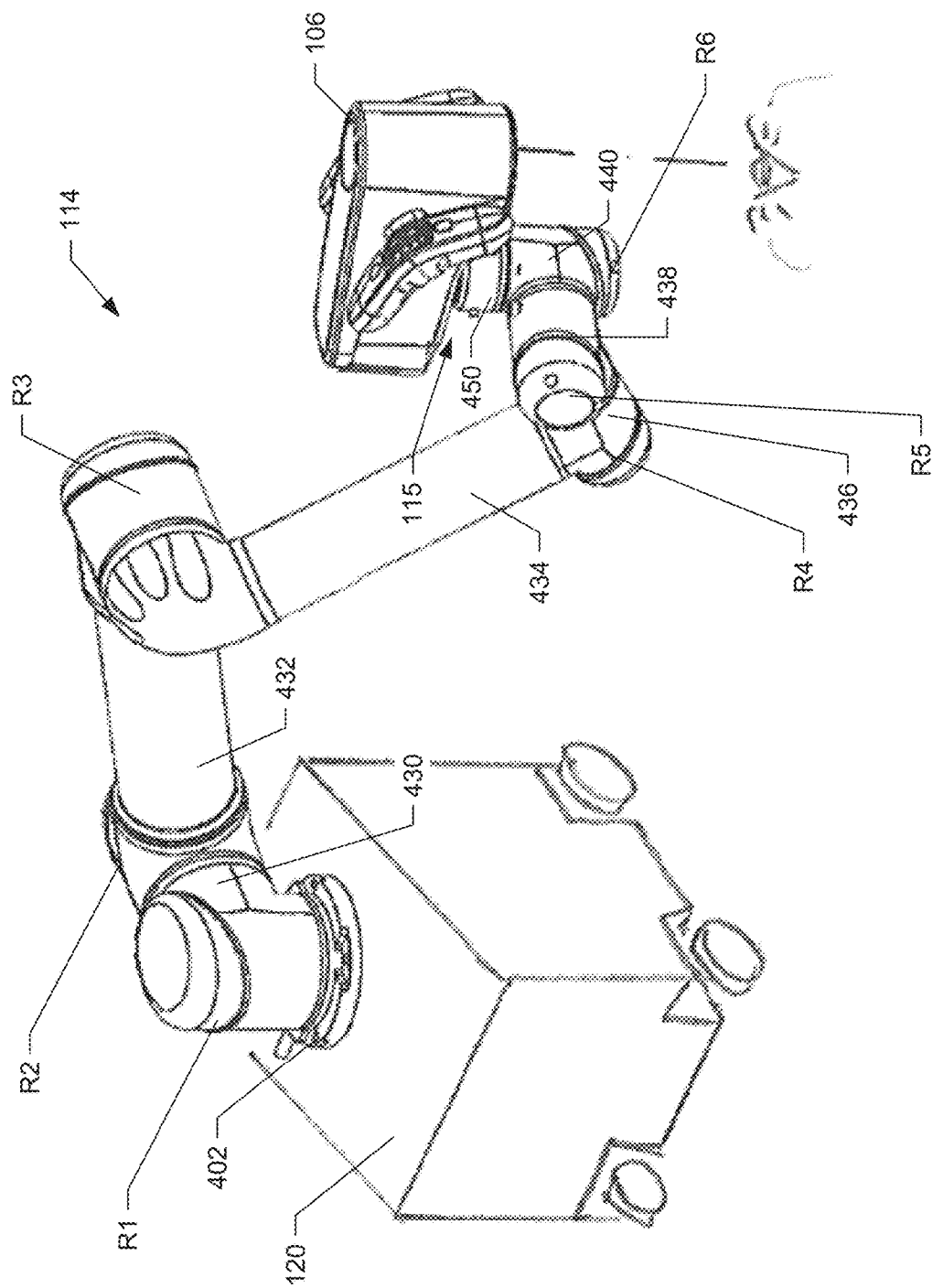
FIG. 5 shows a diagram of the robotic arm of FIG. 4 connected to a cart, according to an example embodiment of the present disclosure.

FIGS. 5 to 10 illustrate example configurations of the robotic arm 114 and the stereoscopic visualization camera 106, according to example embodiments of the present disclosure. FIG. 5 shows a diagram of the robotic arm 114 connected to the cart 120 via the flange 402. In this example, the stereoscopic visualization camera 106 is connected directly to the connector 450. In this embodiment, the connector 450 and/or the stereoscopic visualization camera 106 may include the sensor 115 of FIGS. 1-3 for sensing translational and/or rotational force/motion imparted by an operator on the stereoscopic visualization camera 106. If the connector 450 includes the sensor 115, the output force/motion data may be transmitted through the robotic arm 114 to a controller. If, for example, the sensor 115 is located on the stereoscopic visualization camera 106, the output data may be transmitted with control data to a separate controller. In some embodiments, a controller may be provided in the cart 120 or separately at a server.

Figure 6:
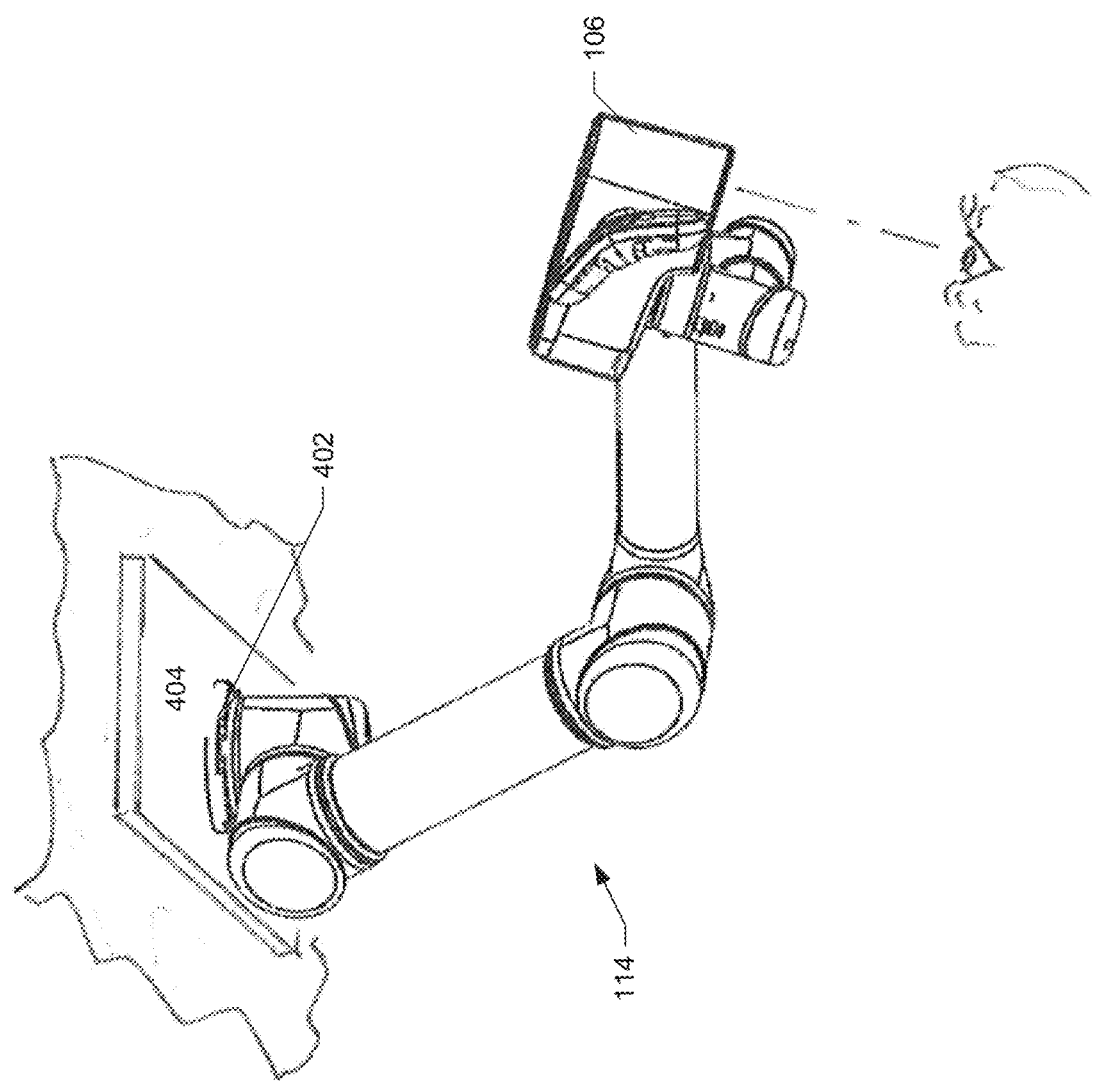
FIG. 6 shows a diagram where the robotic arm of FIG. 4 is mounted to a ceiling plate, according to an example embodiment of the present disclosure.

FIG. 6 shows an embodiment where the robotic arm 114 is mounted to a stationary structure 404 that is a ceiling plate. The robotic arm may be suspended from the ceiling of an operating room via the flange 402 to reduce floor space clutter. The robotic arm 114, including the joints, can be positioned above and traversed from the area where surgical activity is being performed, out of the way of the surgeon and operating room staff, yet still providing functional positioning and/or orientating of the camera 106 while providing a clear view of the display monitors (e.g., display monitors 122A-E as previously described in relation to FIGS. 1-3).

Figure 7:
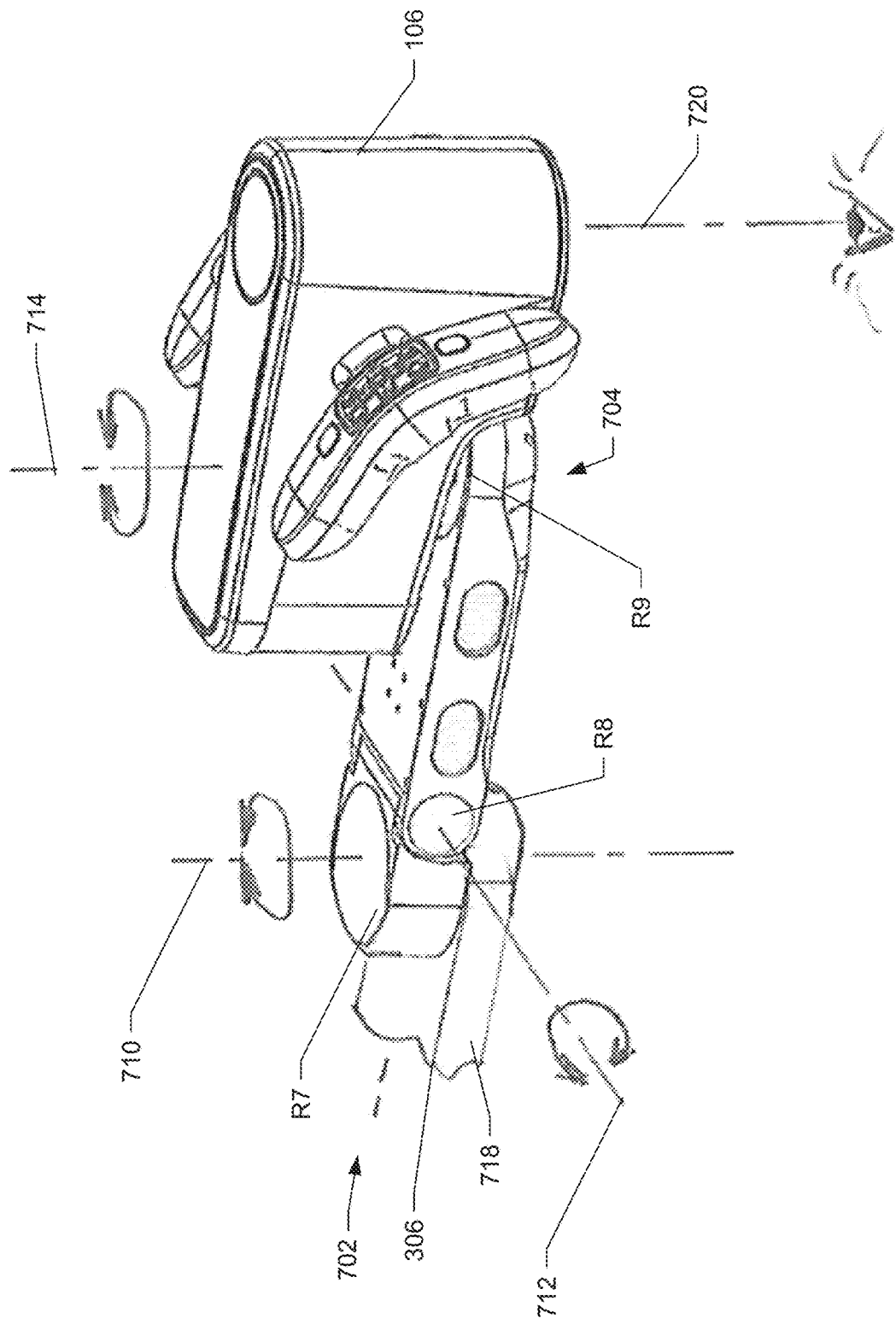
FIG. 7 shows an embodiment of a coupling plate for the robotic arm of FIG. 4, according to an example embodiment of the present disclosure.

FIG. 7 shows an embodiment of the coupling plate 306. In the illustrated example, a first end 702 of the coupling plate 306 is connected to the connector 450 of the robotic arm 114. A second end 704 of the coupling plate 306 is connected to the stereoscopic visualization camera 106. The example coupling plate 306 is configured to provide additional degrees of freedom for moving the stereoscopic visualization camera 106. The coupling plate 306 also extends the maximum reach of the robotic arm 114. The coupling plate 306 may have a length between 10 cm to 100 cm.

The coupling plate 306 may include one or more joints. In the illustrated example, the coupling plate 306 includes joints R7, R8, and R9. The example joints are mechanical joints that provide rotation around respective axes. The joints R7 to R9 may comprise rotatable latching mechanisms that are movable after an operator actuates a release button or lever. Each joint R7 to R9 may have its own release button, or a single button may release each of the joints R7 to R9.

The joints R7 to R9 may be connected together via respective links. In addition, a link 718 is provided for connection to the connector 450 of the robotic arm 114. Joint R7 is configured to rotate around axis 710, while joint R8 is configured to rotate around axis 712, and joint R9 is configured to rotate around axis 714. The axes 710 and 714 are parallel with each other and orthogonal to the axis 712. Joints R7 and R9 may be configured to provide +/−360° rotation. In other examples, joints R7 and R9 may provide +/−90°, +/−180° rotation or +/−270° rotation around the respective axes 710 and 714. Joint R8 may provide +/−90° rotation around the axis 712. In some examples, joint R8 may only be set at +90°, 0°, and −90°.

In some embodiments, joints R7 to R9 may include motors that provide continuous movement. Joints R7 to R9 may also include control devices, such as switches or position sensors that communicate or provide data indicative or a rotational position. In this manner, the joints R7 to R9 may be similar to the joints R1 to R6 of the robotic arm 114 and provide for assisted movement and positioning sensing for feedback control. Power and control for joints R7 to R9 may be provided via wires routed through the robotic arm 114, power/wire connectors within the connector 450, and/or wires external to the robotic arm 114.

Furthermore, FIG. 7 shows an example where the stereoscopic visualization camera 106 is positioned in a horizontal orientation such that an optical axis 720 is provided along a z-axis. The horizontal orientation may be used for imaging patients that are lying down.

Figure 8:
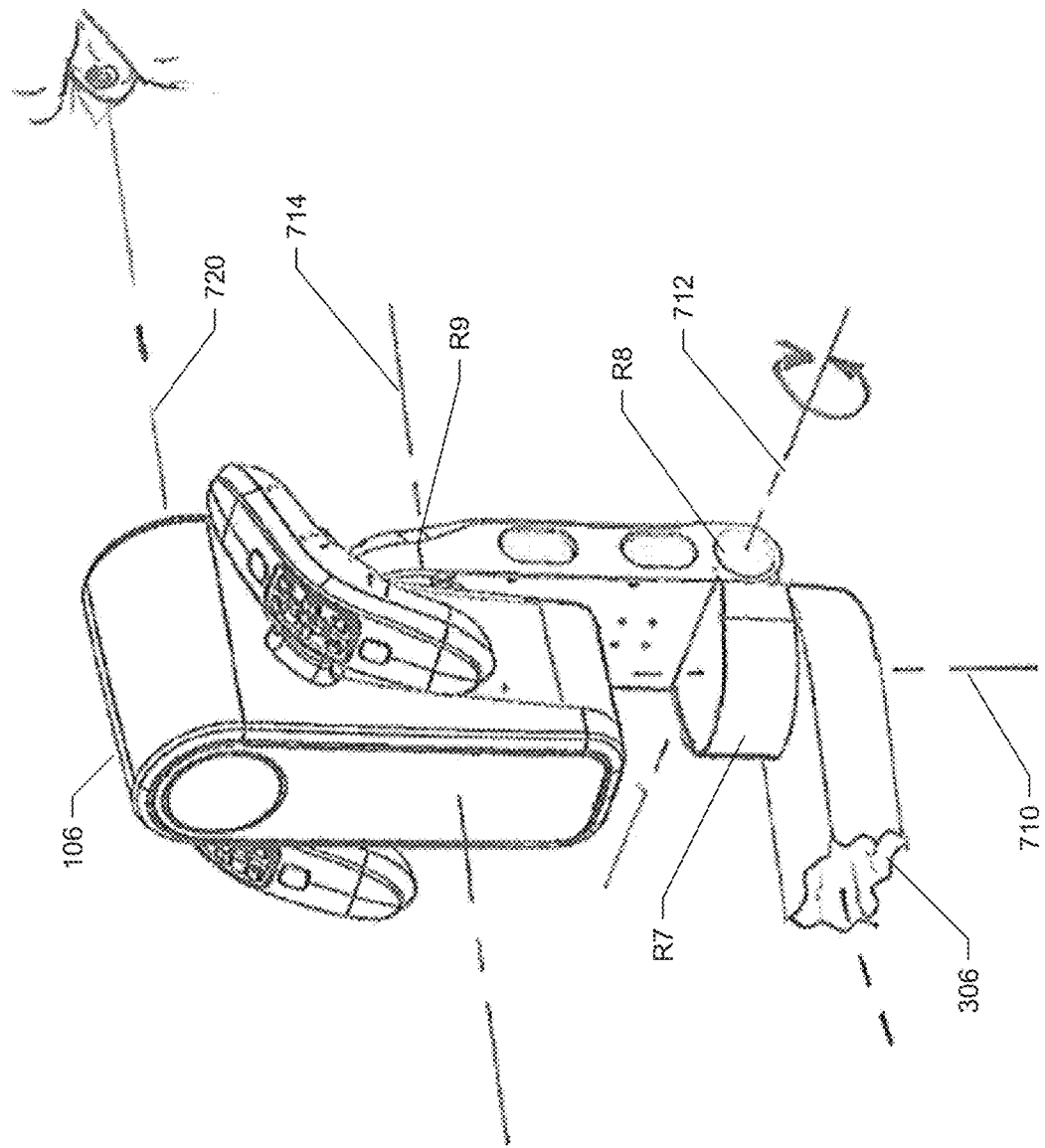
FIGS. 8 to 10 show diagrams of the coupling plate in different rotational positions, according to example embodiments of the present disclosure.

In contrast, FIG. 8 shows an embodiment where joint R8 is rotated by 90° to position the camera 106 in a vertical orientation such that the optical axis 720 is provided along an x-axis or y-axis that is orthogonal to the x-axis. The vertical orientation may be used for imaging patients that are sitting. It should be appreciated that joint R8 enables the stereoscopic visualization camera 106 to quickly be re-orientated between horizontal and vertical positions based on the procedure.

The example sensor 115 may be located at, for example, the connector 450 of the robotic arm (with the connection of the coupling plate 306) and/or at the first end 702 of the coupling plate (at the connection with the connector 450). Alternatively or additionally, the example sensor 115 may be located at, for example, the second end 704 of the coupling plate (at the connection with the camera 106) and/or at the camera 106 at the connection with the second end 704 of the coupling plate 306.

Figure 9:
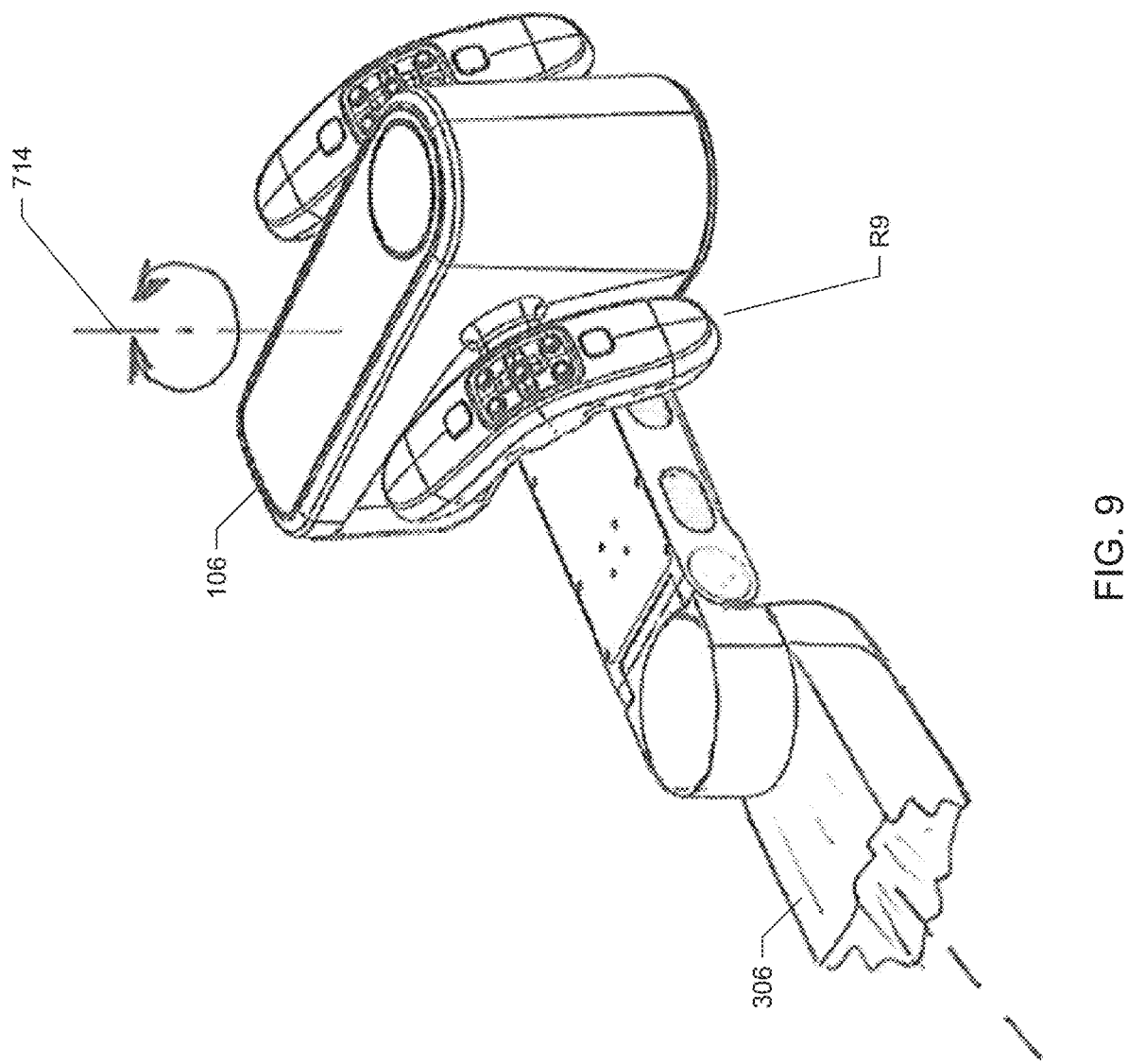
Figure 10:
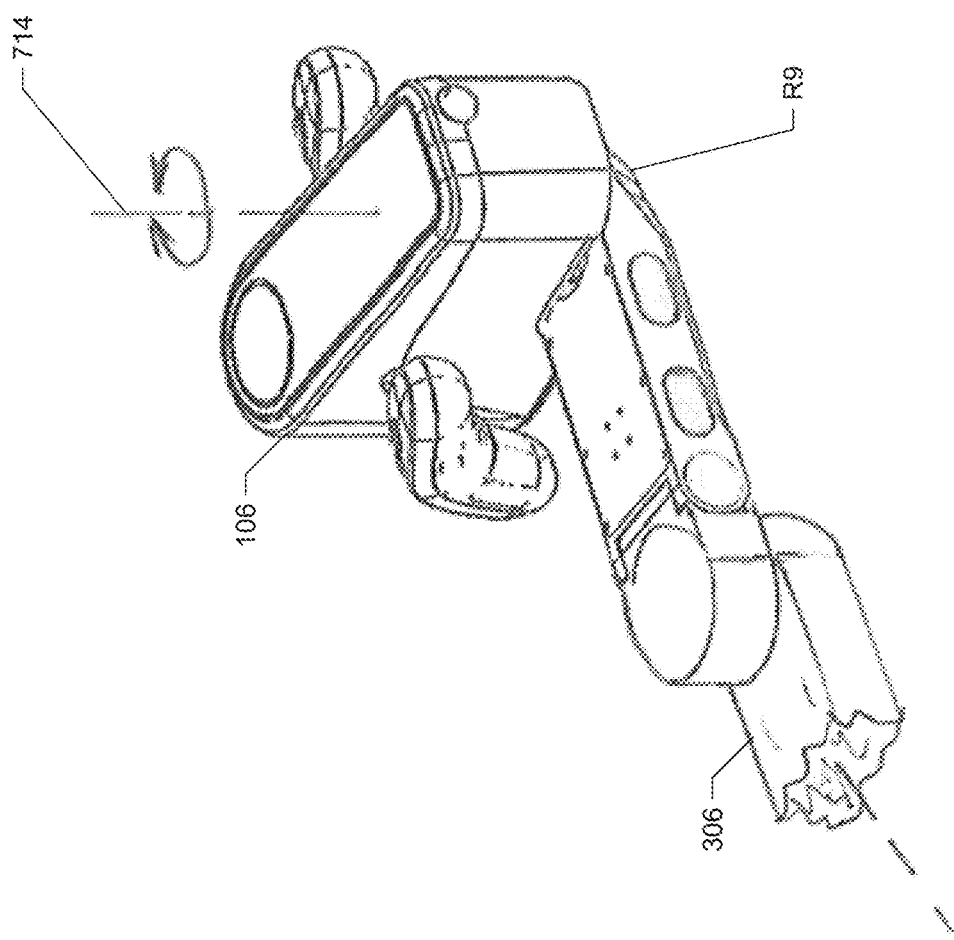

FIG. 9 shows the stereoscopic visualization camera 106 in the horizontal orientation and rotated +90° around the axis 714 of joint R9. FIG. 10 shows an example of the stereoscopic visualization camera 106 in the horizontal orientation and rotated −90° around the axis 714 of joint R9.

As illustrated in FIGS. 3 to 10, the example robotic arm 114 is configured to provide support for the stereoscopic visualization camera 106 and allow for precise positioning and/or orientating and aiming of the camera's optical axis. Since the stereoscopic visualization camera 106 does not have oculars and does not need to be oriented for a surgeon's eyes, there are many desirable positions and/or orientations for imaging that may be achieved that were not previously practical. A surgeon can perform with the view most optimal for a procedure rather than that most optimal for his orientation to the oculars.

The example robotic arm 114, when used with the stereoscopic visualization camera 106, enables a surgeon to see around corners and other locations that are not readily visible. The robotic arm 114 also enables patients to be placed into different positions including supine, prone, sitting, semi-sitting, etc. Accordingly, the robotic arm 114 enables the patient to be placed in the best position for a specific procedure. The example robotic arm 114, when used with the stereoscopic visualization camera 106 can be installed for the least obtrusive position. The arm 114 and camera 106 accordingly provide a surgeon numerous possibilities for visual locations and orientations while being conveniently located and oriented out of the way.

The arrangement of the links and joints of the robotic arm 114 and/or the coupling plate 306, along with the motorized six (or nine) degrees of freedom generally allow the camera 106 to be positioned as desired with the link and joint configuration not unique to the pose of the camera. As discussed in more detail below, the joints and links of the arm 114 and/or the plate 306 may be manually repositioned and/or reoriented without changing the pose or FOV of the camera 106. This configuration allows, for example, an elbow joint to be moved out of an occluding line of sight without changing the view of the surgical site through the camera 106. Further, a control system can determine the location and pose of the camera 106 and calculate and display alternative positions and/or orientations of the robotic arm 114 to, for example, avoid personnel or display occlusion. Use of the various positions and/or orientations of the coupling plate 306 along with an ability of an image processor to flip, invert, or otherwise reorient the displayed image permit even more robot arm 114 positions and/or orientations.

The robotic arm 114 and/or coupling plate 306 is/are generally situated, and the joints are positioned such that joint singularities are avoided in any general movement. The avoidance of joint singularities provides better robotic control of hysteresis and backlash. Further, the lengths and configurations of the links and joints of the robotic arm 114 and/or the coupling plate 306 provide for smooth movement along most any desirable motion paths. For example, repositioning and/or reorienting of the robotic arm 114 enables it to change the direction of the camera 106 view of a target point within a surgical site without changing a focal point, thereby permitting a surgeon to view the same target point from different directions/orientations. In another example, the robotic arm 114 is capable of changing a working distance to a target point without changing a focal point by translating the camera 106 along the line of sight towards or away from the target point. Numerous similar motion paths are attainable as desired using the robotic arm 114 and/or the coupling plate 306 with the stereoscopic visualization camera 106 of the stereoscopic robotic platform 302.

B. Robotic Control Embodiment

The example robotic arm 114 and/or the coupling plate 306 of FIGS. 3 to 10 may be controlled by one or more controllers. FIG. 11 illustrates an embodiment of the stereoscopic robotic platform 302 of FIGS. 1 to 10, according to an example embodiment of the present disclosure. The example stereoscopic robotic platform 302 includes the stereoscopic visualization camera 106.

In the illustrated embodiment, the stereoscopic robotic platform 302 includes a server or processor 1102 that is located remote from the stereoscopic visualization camera 106. The processor 1102 may include, for example, a laptop computer, a workstation, a desktop computer, a tablet computer, a smartphone, etc. configured with one or more software programs defined by instructions stored in the memory 1150 that, when executed by the processor 1102, cause the processor 1102 to perform the operations described here. The example processor 1102 in this example is configured to include (or perform the operations described in connection with) an information processor module 1108, an image sensor controller 1152, and/or a motor and lighting controller 1170.

The processor 1102 is electrically and/or communicatively coupled to an image capture module and motor and lighting module of the stereoscopic visualization camera 106 via a wire harness 1103. In some embodiments, the harness 1103 may be external to the robotic arm 114. In other embodiments, the wire harness 1103 may be internal or routed through the robotic arm. In yet other embodiments, the image capture module 1194 and motor and lighting module 1196 may communicate wirelessly with the processor 1102 via Bluetooth®, for example.

The example processor 1102 is also electrically and/or communicatively coupled to the sensor 115 via the wire harness 1103. The processor 1102 is configured to receive, for example, rotational and/or translational output data from the sensor 115. The data may include digital data and/or analog signals. In some embodiments, the processor 1102 receives a near-continuous stream of output data from the sensor 115 indicative of detected force and/or motion. In other examples, the processor 1102 receives output data at periodic sampled intervals. In yet other examples, the processor 1102 periodically transmits a request message requesting the output data.

In the illustrated example, the processor 1102 is further communicatively coupled to a stereoscopic visualization platform 122 (e.g., at least one of a display monitors 122A-122E0, input devices 1110a, 1110b, and other devices/systems 1104 (e.g., medical imaging devices such as an X-ray machine, a computed tomography ("CT") machine, a magnetic resonance imaging ("MRI") machine, a camera a workstation for storing images or surgical guidelines, etc.). The input device 1110a may include a touch screen device and the input device 1110b may include a foot switch. The touch screen input device 1110a may be integrated with the display monitor 512 and/or provided as a separate device on, for example, the cart 120 of FIG. 3. The example stereoscopic visualization platform 122 is configured to display one or more user interfaces that include a stereoscopic video (or separate two-dimensional left and right videos) of a target surgical site recorded by the stereoscopic visualization camera 106.

The touch screen input device 1110a is configured to provide one or more user interfaces for receiving user inputs related to the control of the stereoscopic visualization camera 106, the coupling plate 306, and/or the robotic arm 114. The input device 1110a may include one or more graphical control buttons, sliders, etc. that are configured to enable an operator to specify, set, or otherwise provide instructions for controlling a working distance, focus, magnification, source and level of illumination, filters, and/or digital zoom of the stereoscopic visualization camera 106. The input device 1110a may also include one or more control buttons to enable an operator to select surgical guidance graphics/text, a video and/or an image for fusing and/or otherwise superimposing on the displayed stereoscopic video displayed on the display monitor 512. The input device 1110a may also include a user interface that is configured to enable an operator input or create a surgical procedure visualization template. The input device 1110a may further include one or more control buttons for controlling the robotic arm 114 and/or the coupling plate 306, including options for controlling operational parameters such as speed, motion, deployment/stowing, calibration, target-lock, storing a view position, and/or changing or inputting a new orientation of the camera 106. The user interface controls for the robotic arm 114 and/or the coupling plate 306 may include controls for moving the camera 106, which are translated into commands for the individual joints R1 to R9. Additionally or alternatively, the user interface controls for the robotic arm 114 and/or the coupling plate 306 may include controls for moving each of joints R1 to R9 individually. Inputs received via the input device 1110a are transmitted to the processor 1102 for processing.

The input device 1110b may include, for example, a food pedal configured to receive inputs for controlling a position of the stereoscopic visualization camera 106, the coupling plate 306, and/or the robotic arm 114. For example, the foot plate input device 1110b may include controls for moving the camera 106 along the x-axis, the y-axis, and/or the z-axis. The foot plate input device 1110b may also include controls for storing a position of the camera 106 and/or returning to a previously stored position. The foot plate input device 1110b may further include controls for changing a focus, zoom, magnification, etc. of the camera 106.

In other embodiments, the stereoscopic robotic platform 302 may include additional and/or alternative input devices 1110a-1110b, such as a joystick, mouse, or other similar 2D or 3D manual input device. The input devices 1110a-1110b are configured to provide inputs similar to an X-Y panning device, with additional degrees of freedom resulting in flexibility of system motion. Input devices with 3D capabilities, such as a 3D mouse or six-degree of freedom controller are well suited for flexible and convenient input commands. A major benefit of these user control devices is that the surgical image can be easily viewed while the motion is occurring. Further, a surgeon can view what is happening around the entire surgical and nearby sites to avoid, for example, bumping the camera 106 into surgical staff and/or nearby equipment.

Optionally, the input devices 1110a-1110b may include a head, eye, or glasses-mounted tracking device, a voice recognition device, and/or a gesture input device. These types of input devices 1110a-1110b facilitate "hands-free" operability such that an operator does not need to touch anything with their sterile gloves. A gesture-recognizing control may be used, where certain operation hand motions are recognized and translated into control signals for the camera 106, the coupling plate 306, and/or the robotic arm 114. A similar function is provided by a voice-recognition device, where a microphone senses a command from an operator, such as "move the camera left", recognizes the speech as a command, and converts it into appropriate camera and/or robot control signals. Alternate embodiments include an eye tracking device that is configured to determine a position of an operator's eyes with respect to a 3D display, and can adjust the view depending on where in the displayed scene the operator is looking.

Other embodiments include a device configured to track a position of an operator's head (via for example a trackable target or set of targets that are mounted on an operator's 3D glasses) in a frame of reference and a footswitch to activate "head tracking". The example tracking input device is configured to store a starting position of an operator's head at activation time and then detects head position continually at some short time interval. The tracking input device in conjunction with the processor 1102 may calculate a movement delta vector between a current position and the starting position and convert the vector into corresponding robotic arm or camera lens movements. For example, a tracking input device 1110a and the processor 1102 may convert left/right head movements into robotic arm movements such that an image onscreen moves left/right. The tracking input device 1110a and the processor 1102 may also convert up/down head movements into robotic arm or camera lens movements such that an image onscreen moves up/down, and may convert forward/back head movements into robotic arm or camera lens movements such that an image onscreen zooms in/out. Other movement conversions are possible, for example, by converting head rotation into a "lock-to-target" motion of the robotic arm 114. As described here, lock-to-target is configured to maintain a focal point of the robotic platform 516 on the same point in a scene or FOV to within some tolerance and pivot the robotic arm 114 (and hence the view) in a direction which mimics the head movement of an operator.

Prior to certain surgical procedures, a surgical plan is created that establishes desired paths for instruments and visualization. In some embodiments, the input device 1410 is configured to follow such a predetermined path with little further input from an operator. As such, the operator can continue operating while the view of the surgical site is automatically changing as pre-planned. In some embodiments, the surgical plan may include a set of pre-planned waypoints, corresponding to camera positions, magnification, focus, etc. An operator may actuate the input device 1410 to progress through the waypoints (causing the processor 1102 to move the robotic arm 114, the coupling plate 306, and/or the camera 106 as planned) as the surgical procedure progresses.

In the illustrated embodiment, the example sensor 115 is an input device. The sensor 115 is configured to detect an operator's movement or force on the stereoscopic visualization camera 106 and convert the detected force/movement into rotational and/or translational data. The sensor 115 may include a motion-anticipation input device, such as a six-degrees-of-freedom haptic force-sensing module or an opto-sensor (e.g., force/torque sensor), that enables the robotic arm 114 to respond electromechanically to an operator's gentle push on the camera 106. The opto-sensor may include an electro-optical device configured to transform applied forces and/or torques into electrical signals, thereby enabling a desired force/torque input by an operator to be sensed and transformed into a motion request that is provided in the sensed linear and/or rotational direction(s). In other embodiments, other sensors types may be used for the sensor 115. For example, the sensor 115 may include a strain gauge or piezoelectric device that is configured to sense a haptic request from an operator.

In an embodiment, a surgeon holds one or more of the control arms 304 and actuates or pushes a release button (which may be located on one or both of the control arms 304). Actuation of the release button causes the camera 106 to transmit a message to the processor 1102 indicative that an operator desires to begin an "assisted-movement" mode. The processor 1102 configures the robotic arm 114 and/or the coupling plate 306 to enable the surgeon to gently steer the camera 106 in a desired direction. During this movement, the processor 1102 causes the robotic arm 114 and/or the coupling plate to move the camera 106 in a "power steering" manner, safely supporting its weight and automatically determining which joints should be activated and which should be braked in a coordinated manner to achieve the surgeon's desired movement.

Figure 11:
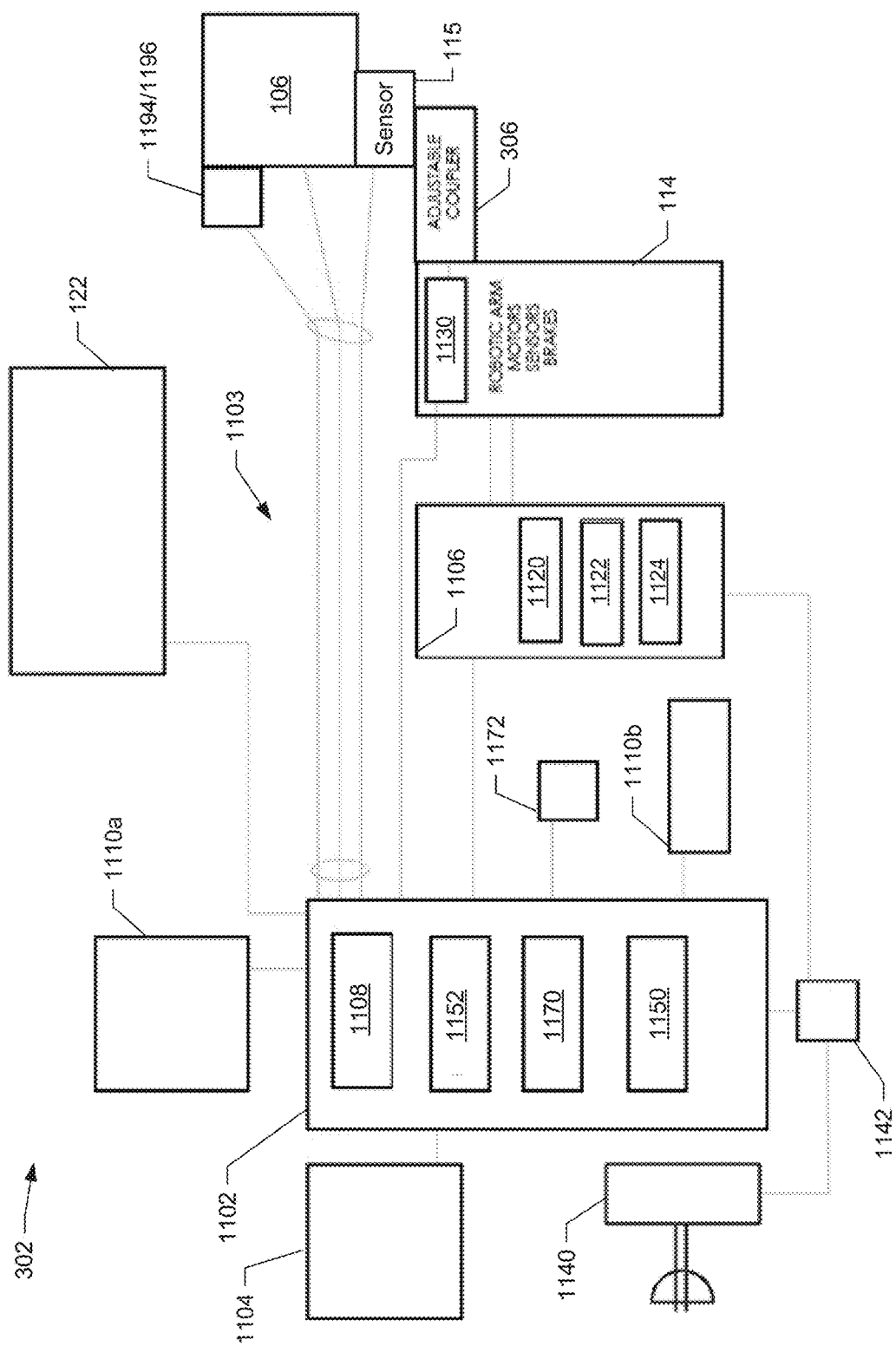
FIG. 11 illustrates an embodiment of the stereoscopic robotic platform of FIGS. 1 to 10, according to an example embodiment of the present disclosure.

In the illustrated example, the stereoscopic robotic platform 302 of FIG. 11 includes a robotic arm controller 1106 that is configured to control the robotic arm 114 and/or the coupling plate 306. The robotic arm controller 1106 may include a processor, a server, a microcontroller, a workstation, etc. configured to convert one or more messages or instructions from the processor 1102 into one or more messages and/or signals that cause any one of joints R1 to R9 to rotate. The robotic arm controller 1106 is also configured to receive and convert sensor information, such as joint position and/or speed from the robotic arm 114 and/or the coupling plate 306 into one or more messages for the processor 1102.

In some embodiments, the robotic arm controller 1106 is configured as a stand-alone-module located between the processor 1102 and the robotic arm 114. In other embodiments, the robotic arm controller 1106 may be included within the robotic arm 114. In yet other embodiments, the robotic arm controller 1106 may be included with the processor 1102.

The example robotic arm controller 1106 includes one or more instructions stored in a memory 1120 that are executable by a robotic processor 1122. The instructions may be configured into one or more software programs, algorithms, and/or routines. The memory 1120 may include any type of volatile or non-volatile memory. The example robotic processor 1122 is communicatively coupled to the processor 1102 and is configured to receive one or more messages related to operation of the robotic arm 114 and/or the coupling plate 306. The example robotic processor 1120 is also configured to transmit to the processor 1102 one or more messages that are indicative of positions and/or speeds of joints R1 to R9. The one or more messages may also be indicative that a joint has reached a travel-stop or is being prevented from moving.

The example processor 1102 is configured to determine which joints R1 to R9 are powered in a coordinated manner such that a totality of all motions of all the joints results in the desired image motion at the camera 106. In a "move the camera left" example there may be complex motions of several joints which cause the camera's surgical image to appear to simply and smoothly translate to the left, from a relative viewpoint of a surgeon. It should be noted that in the "move the camera left" example, depending on how the camera 106 is connected to the robotic arm 114 through the coupling plate 306, the control signals to specific joints may be drastically different depending on the position/orientation.

The memory 1120 may include one or more instructions that specify how joints R1 to R9 are moved based on a known position of the joints. The robotic arm controller 1106 is configured to execute the one or more instructions to determine how instructed camera movement is translated into joint movement. In an example, the robotic arm controller 1106 may receive messages from the processor 1102 indicative that the stereoscopic visualization camera 106 is to move downward along a z-axis and move sideward in an x-y plane. In other words, the processor 1102 transmits indicative of inputs received via the input devices 1110a-1110b regarding desired movement of the camera 106. The example robotic arm controller 1106 is configured to translate the vectors of movement in 3-dimensional coordinates into joint position movement information that achieves the desired position/orientation. The robotic arm controller 1106 may determine or take into account the current location of the links and joints of the robotic arm 114 and/or the coupling plate 306 (and/or a position/orientation of the camera 106) in conjunction with the desired movement to determine a movement delta vector. In addition, the robotic arm controller 1106 may perform one or more checks to ensure the desired movement does not cause the camera 106 to enter into or progress close to a restricted area, as specified by one or more three-dimensional boundaries that are defined in the same coordinate system as the arm 114 and coupling plate 306. Areas close to a boundary may specify a reduced scale factor that is applied by the robotic arm controller 1106 when movement signals are sent to the joints, which causes the joints to move slower as the robotic arm 114 approaches a boundary, and not move any further past a boundary.

After the boundary checks are performed, the robotic arm controller 1106 uses the movement delta and the current position/orientation of each of joints R1 to R9 to determine an optimal or near optimal movement sequence for rotating one or more of the joints to cause the robotic arm 114 to move the camera 106 into the specified location. The robotic arm controller 1106 may use, for example, an optimization routine that determines a minimal amount of joint movement needed to satisfy the movement delta vector. After the amount of joint movement is determined, the example robotic arm controller 1106 is configured to send one or more messages (indicative of an amount of rotation and speed of rotation, taking into account any scale factors) to a motor controller 1124. The robotic arm controller 1106 may transmit a sequence of messages to cause the robotic arm 114 and/or coupling plate 306 to move in a defined or coordinated sequence. The sequence of messages may also cause a change in joint speed as, for example, the robotic arm 114 approaches a virtual or physical boundary.

The example motor controller 1124 is configured to translate or covert the received messages into analog signals, such as pulse-width modulated ("PWM") signals that cause one or more of joints R1 to R9 to rotate. The motor controller 1124 may, for example, select the input line to the appropriate joint motor, where a pulse duration is used for controlling a duration of time that the motor rotates and a frequency, duty cycle, and/or amplitude of the pulse is used to control rotation speed. The motor controller 1124 may also provide power for the joint motors and corresponding joint sensors.

In some embodiments, the robotic arm controller 1106 in combination with the motor controller 1124 is configured to receive or read joint sensor position information and determine, through kinematics, the location and orientation of the robotic joints and camera 106. Each joint R1 to R9 may include at least one sensor that detects and transmits data indicative of joint position, joint rotational speed, and/or joint rotational direction. In some embodiments, the sensors transmit only position information, and speed/direction are determined by the robotic arm controller 1106 based on differences in the position information over time. The robotic arm controller 1106 may transmit the sensor data to the processor 1102 for determining movement information.

The robotic arm controller 1106 receives movement instructions from the processor 1102 and determines, through Jacobian, forward, and/or inverse kinematics, which motors and joints should be activated, how fast and how far, and in what direction. The robotic arm controller 1106 then sends the appropriate command signals to motor power amplifiers in the motor controller 1124 to drive the joint motors in the robotic arm 114.

The example robotic arm 114 receives appropriate motor power signals and moves accordingly. Sensors and brakes in the robotic arm 114 react to the various operations and feedback information from the robotic arm controller 1106. In some embodiments, the robotic arm 114 is mechanically and communicatively connected to the coupling plate 306, which transmits coupler status and orientation information to the robotic arm controller 1106.

In some embodiments, the example robotic arm 114 of FIG. 11 includes a coupler controller 1130. The example coupler controller 1130 is configured to bypass the robotic processor 1106 and relay control information between the processor 1102 and the coupling plate 306. The coupler controller 1130 may receive messages from the processor 1102 and correspondingly cause joints R7 to R9 rotate on the coupling plate 306. The coupler controller 1130 may also receive sensor information regarding joint position and/or speed and transmit one or more messages to the processor 1102 indicative of the joint position and/or speed. In these embodiments, the processor 1102 may transmit messages for controlling the robotic arm 114 and separate messages for the coupling plate 306.

In some embodiments, the robotic arm controller 1106 is configured to determine how joints R7 to R9 are to move. However, if the coupling plate 306 is not communicatively coupled directly to the robotic arm 114, the robotic processor 1106 may transmit the movement signals to the coupler controller 1130 via the processor 1102. In instances where at least some operators of the robotic processor 1106 are located with the processor 1102, the coupler controller 1130 receives movement commands or signals from the processor 1102 in conjunction with the robotic arm 114 receiving movement commands or signals from the processor 1102.

In the illustrated embodiment of FIG. 11, the example stereoscopic visualization camera 106, the processor 1102, the coupling plate 306, the robotic arm 114, the robotic arm controller 1106, and/or the input devices 1110a-1110b receive power via an input power module 1140. The example input power module 1140 includes a power supply (such as power from a wall outlet) and/or an isolation transformer to prevent powerline anomalies from disrupting system performance. In some instances, the power supply can include a battery power supply.

The stereoscopic robotic platform 302 may also include an emergency stop switch 1142 that is configured to immediately cut off power. The switch 1142 may only cutoff power to the robotic arm 114 and/or the coupling plate 306. The processor 1106 may detect activation of the emergency stop switch 1142 and cause joint brakes to engage to prevent the robotic arm 114 from falling. In some instances, the robotic arm 114 is configured to activate the joint brakes after detecting a loss of power. In some embodiments, joints R1 to R6 of the robotic arm 114 are configured to slip if a force above a threshold is applied, thereby enabling an operator to quickly move the arm out of the way in an emergency, with or without power.

In some embodiments, the example processor 1102 is configured to display one or more graphical representations of the robotic arm 114, the coupling plate 306, and/or the stereoscopic visualization camera 106. The processor 1102 may cause the graphical representation to be displayed in one or more user interfaces that provide control for the robotic arm 114, the coupling plate 306, and/or the camera 106. The processor 1102 may position and orient the graphical representation to reflect the current position of the robotic arm 114, the coupling plate 306, and/or the camera. The processor 1102 uses, for example, feedback messages from the robotic arm controller 1106 to determine which joints in the graphical representation are to be rotated, thereby changing the orientation and/or position of the display device. In some instances, the processor 1102 is configured to receive user input via the graphical representation by, for example, an operator moving the links, joints, or camera 106 in the graphical representation to a desired position. In the case of movement of the stereoscopic visualization camera 106, the processor 1102 may transmit the new coordinates corresponding to where the camera was moved. In the case of moved joints or links, the processor 1102 may transmit to the robotic arm controller 1106 messages indicative of joint rotation and/or positions of links.

C. Robotic Arm and Stereoscopic Camera Calibration Embodiment

As discussed above, the example stereoscopic visualization camera 106 is configured to provide high-resolution stereoscopic video images of a target surgical site at different magnifications. As part of the stereoscopic robotic platform 302, the stereoscopic visualization camera 106 operates in connection with the robotic arm 114 and/or the coupling plate 306 for precise and clear changes to image focus, working distance, magnification, etc. To accomplish the image acquisition flexibility, the stereoscopic robotic platform 302 is configured to operate one or more calibration, initialization, and/or reset routines. In some embodiments, the stereoscopic visualization camera 106, the robotic arm 114, the coupling plate 306, or more generally, the stereoscopic robotic platform 302 is calibrated during manufacture and/or after installation. Calibration of the camera 106 with the robotic arm 114 provides positioning information of the camera 106 relative to the robotic arm 114 and operator space. After power-up of the stereoscopic robotic platform 302, in some embodiments, the camera 106 and/or the robotic arm 114 is configured to perform further calibration/initialization to measure and verify a location and orientation of the camera 106 at that time.

The example processor 1102 is configured to store results from the calibration (e.g., calibration data), in, for example, the memory 1150 and/or the memory 1120 of FIG. 11. The calibration results may be stored to calibration registers and/or lookup tables ("LUTs") in the memories 1150 and/or 1120. The stored calibration data relates or maps optical, functional, and/or performance characteristics to attributes of the camera 106, the robotic arm 114, and/or the coupling plate 306 that are adjustable, measurable, and/or verifiable by an operator or by the processor 1102. For example, a working distance actuator motor encoder position for the main objective assembly 702 (of FIG. 5) is mapped in a LUT to a working distance. In another example a zoom lens axial position along a linear encoder for the zoom lens assembly 716 is mapped in a LUT to the magnification level. For each of these examples, the example processor 1102 is configured to determine the proper level of an encoder characteristic, adjust, and verify that the characteristic provides the specified or desired working distance and/or magnification. In some embodiments, LUTs may be compound, where multiple performance characteristics are mapped to multiple platform 516 attributes for overall control of all relevant aspects of the camera 106, the robotic arm 114, and/or the coupling plate 306.

The combination of a robotic arm 114 and the example stereoscopic visualization camera 106 provides highly accurate position, direction, and/or orientation information of the target view with respect to a frame of reference of the robotic arm 114. The following sections describe how the stereoscopic visualization camera 106 is calibrated to define a visual tip. After a visual tip is determined, the stereoscopic visualization camera 106 is registered to a frame of reference of the robotic arm 114 and/or the coupling plate 306. Accordingly, after calibration and registration, a stereoscopic view of a surgical site is unified with the integrated control of the stereoscopic visualization camera 106 combined with the position, direction, and orientation control of the robotic arm 114 and/or coupling plate 306.

In some embodiments, the example processor 1102 of FIG. 11 is configured to integrate a registration of stereoscopic visualization camera 106, including its visual tip, precisely with a position, direction, and/or orientation calibration of the robotic arm 114 to define a unified position, direction, and/or orientation awareness of acquired stereoscopic images and all points therewithin, with respect to a prescribed coordinate frame. The example processor 1102 is configured to use intrinsic visual imaging data from the stereoscopic visualization camera 106 to coordinate or direct the physical positioning and/or orientating of the robotic arm 114 to provide visualization, as desired by an operator. In addition, such direction and coordination provided by the processor 1102 is provided to maintain preferred characteristics of the visualization such as focus, working distance, pre-defined positioning, orientating, etc.

In some embodiments, calibration of the stereoscopic visualization camera 106, the robotic arm 114, and/or the coupling plate 306 generally includes (i) determining and/or measuring inaccuracies of functional parameters of the stereoscopic robotic platform 302 that affect stereoscopic images; (ii) calibrating or adjusting, the stereoscopic robotic platform 302 to minimize the inaccuracies in the stereoscopic images at or below a desired level; (iii) verifying that the adjustments have been made within a desired level of calibration accuracy through simultaneous comparisons of the dual channels of the stereoscopic images to each other or calibration templates; and (iv) using the stereoscopic robotic platform 302 in the performance of its tasks, where a level of the accuracy of the calibration is detectable and maintained.

In an alternative embodiment, the robotic arm 114 is provided with one or more fixed calibration fiducials that are used to precisely calibrate a physical relationship of the joint and links of the robotic arm 114 to one another as well as to calibrate a relationship of the visual tip of the camera 106 to the robotic arm 114 and/or an initial pose configuration. The robotic platform fixed calibration fiducials can be used to register or integrate the robotic arm 114 with an external environment, such as an operating room theater or with a patient or target space within an external environment. The fixed calibration fiducials can either include a dedicated attachment to an external portion of a body of the robotic arm 114 or a combination of known external features of the robotic arm 114, such as mounting points, joints, corners, or the like.

1. Calibration of the Robotic Arm Embodiment

After the stereoscopic visualization camera 106 is calibrated, as discussed above, it may be connected to the robotic arm 114 and/or the coupling plate 306. As described below, precise knowledge of the working distance with respect to focal distance Z, provided by the stored calibration parameters, is used by the example processor 1102 and/or the robotic processor 1122 for determining a position and/or orientation for the stereoscopic visualization camera 106. The combination of the stereoscopic visualization camera 106 with the robotic arm is configured to provide seamless transitions of various working distances while holding a focus or view of a target surgical site.

The calibration procedure for the robotic arm 114, described below, may be executed regardless of a robotic arm type. For example, the calibration procedure may be performed for an articulated robotic system that includes mechanical links connected to each other via rotary joints, numbering from simple one or two links and joints, to joint structures comprising six or more joints. The calibration procedure may also be performed for a Cartesian robotic system that comprises a gantry with linear joints, which uses a coordinate system with X, Y and Z directions. A final joint of a Cartesian robotic system may comprise a wrist type swiveling joint. The calibration procedure may further be performed for a cylindrical robotic system that comprises a rotary joint at its base and one or more additional rotary and/or linear joints to form a cylindrical workspace. Moreover, the calibration procedure may be performed for a polar robotic system that comprises an arm connected to a base via a joint that may operate in more than one rotational axis and further comprises one or more linear or wrist joints. The calibration procedure may additionally be performed for a Selective Compliance Assembly Robot Arm ("SCARA") system that comprises a selectively compliant arm operated in a primarily cylindrical fashion, which is used for assembly applications.

Figure 12:
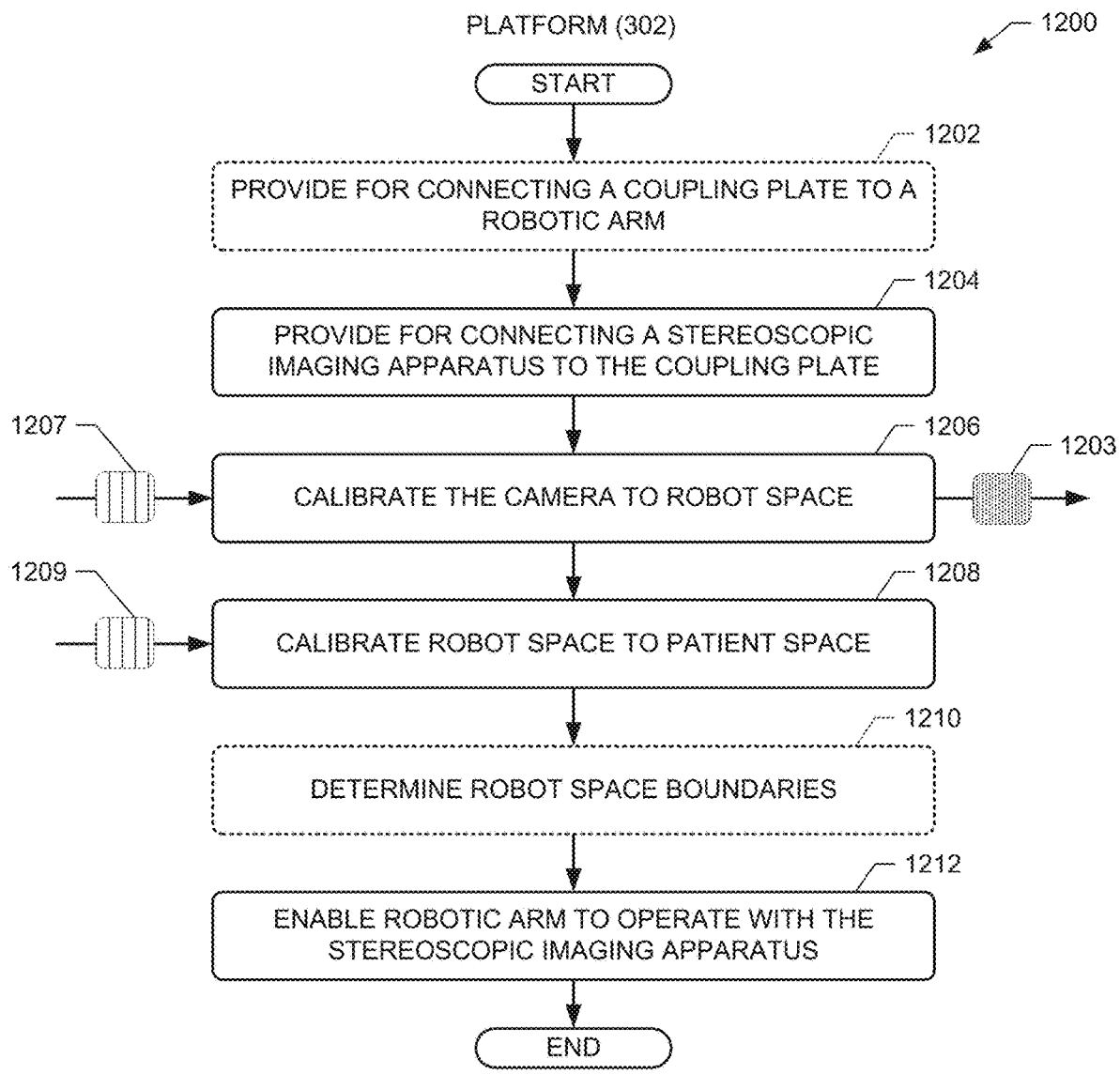
FIG. 12 illustrates an example procedure or routine for calibrating the robotic arm, according to an example embodiment of the present disclosure.

FIG. 12 illustrates an example procedure 1200 or routine for calibrating the robotic arm 114, according to an example embodiment of the present disclosure. Although the procedure 1200 is described with reference to the flow diagram illustrated in FIG. 12, it should be appreciated that many other methods of performing the steps associated with the procedure 1200 may be used. For example, the order of many of the blocks may be changed, certain blocks may be combined with other blocks, and many of the blocks described are optional. Further, the actions described in procedure 1200 may be performed among multiple devices including, for example the optical elements, the image capture module 1194, the motor and lighting module 1196, the information processor module 1108 of the example stereoscopic visualization camera 106 of FIG. 10 and/or joints R1 to R9 and robotic arm controller 1106 of FIG. 11. For example, the procedure 4800 may be performed by a program stored in the memory 1120 of the robotic arm controller 1106.

In some embodiments, the coupling plate 306 is connected to the robotic arm 114 (block 1202). If a coupling plate 306 is not used, the stereoscopic visualization camera 106 is connected directly to the connection or a coupling interface (e.g., connector 450) of the robotic arm 114. If the coupling plate 306 is used, the stereoscopic visualization camera 106 is connected to the coupling plate (block 1204). As discussed above, first end 702 of the coupling plate 306 is connected to the robotic arm 114 and the second end 704 of the coupling plate 306 is connected to the stereoscopic visualization camera 106.

After the example stereoscopic visualization camera 106 is connected to the robotic arm 114, the example processor 1102 and/or the robotic arm controller 1106 are configured to calibrate the camera and its view vector into a coordinate system originated around the stationary base 404 of the robotic arm 114 (block 1206). The coordinate system is referred to herein as "robot space" or "robotic space". During this calibration step, known movements to the robotic arm 114 are used by the processor 1102 and/or the robotic arm controller 1106 to determine an orientation and a location of a view vector and object plane of the camera 106 during visualization of a target surgical site.

In some embodiments, the mechanical features of the camera 106, the coupling plate 306, and the robotic arm 114 exist such that, when mechanically connected together, the relationship between the camera 106, the coupling plate 306, and the robotic arm 114 is uniquely determined and known. In these embodiments, the processor 1102 and/or the robotic arm controller 1106 determine the position, direction, and/or orientation of the view vector from the known mechanical geometry of the camera 106, the coupling plate 306, and the robotic arm 114.

In other embodiments where the mechanical features do not exist, the example processor 1102 and/or the robotic arm controller 1106 are configured to perform a routine to accurately determine a spatial relationship between the camera 106 and the robotic arm 114 in robot space. The processor 1102 and/or the robotic arm controller 1106 move the stereoscopic visualization camera 106 to a start position, which may include a stow position, a re-orientation position, or a surgical position. The stereoscopic visualization camera 106 then moves the camera from the start position to a position that approximately visualizes a calibration target located on the stationary base 404 of the robotic arm 114. The calibration target may be located, for example, at a convenient area of the cart 120 in a position within the motion sphere of the robotic arm 114. Some examples of the calibration target include, for example, small spheres or other uniquely recognizable objects that can be located relative to each other (in two-dimensional or stereoscopic images) in a unique, known orientation. The coordinates of the spheres are fixed and known with respect to the cart 120 and stationary base 404, and are hence known in robot space. The processor 1102 and/or the robotic arm controller 1106 are configured to store the coordinates to, for example, the memory 1120.

During the calibration, the processor 1102 and/or the robotic arm controller 1106 receive view vector data 1207 regarding working distance, magnification, stereoscopic optical axis, and/or IPD. The stereoscopic visualization camera 106 is set to visualize the spheres at the calibration target simultaneously and determine their position through the use of parallax in the stereoscopic image. The processor 1102 and/or the robotic arm controller 1106 records the positions of the spheres in an initial coordinate system, for example, X, Y, and Z with respect to a fiducial in the camera 106 (i.e. "camera space"). The X, Y, Z position may correspond to an origin location, and be defined in a file or LUT as being the origin or having other known coordinate values. The processor 1102 and/or the robotic arm controller 1106 also use output data from joint sensors to determine position and orientation of the joints and links in the robotic arm 114. The processor 1102 and/or the robotic arm controller 1106 also receive position information to determine a position and orientation of the coupling plate 306. Together, the position and orientation of the robotic arm 114 and the coupling plate 306 enable the processor 1102 and/or the robotic arm controller 1106 to determine a pose of the camera 106. The processor 1102 and/or the robotic arm controller 1106 are configured to perform a coordinate transformation between the camera space and robot space based on the positions of the spheres of the calibration target as recorded by the camera, and as the positions of the robotic arm 114 and/or coupling plate 306. The processor 1102 and/or the robotic arm controller 1106 may store the coordinate transformation to the LUT 1203, a different LUT for the robotic arm 114, and/or one or more calibration registers.

In some embodiments, the camera 106 is moved to record images of multiple calibration targets located either on a cart 120, a ceiling, a wall, and/or within a surgical area. Each of the calibration targets may have a unique orientation that enables it physical X, Y, Z location to be identified. The processor 1102 and/or the robotic arm controller 1106 perform additional coordinate transformations for each of the calibration targets and store the transformations to one or more LUTs and/or registers.

In other embodiments, the processor 1102 and/or the robotic arm controller 1106 may use alternative methods to calibrate the camera 106 to robot space. In this context, "calibration" is taken to mean "registration", where the processor 1102 and/or the robotic arm controller 1106 are configured to calculate registration over a wide space in which the registration may vary. For example, a system can be used where a separate stereoscopic camera is used to observe and locate calibration targets on the cart 120 as well as similar calibration targets which are installed on the camera 106 and/or on a patient or surgical bed. The processor 1102 and/or the robotic arm controller 1106 are configured to model and track the camera 106, which is modeled and tracked as a surgical instrument with a view vector and working distance. The view vector and working distance define parameters for accurately visualizing a target surgical site. In these other embodiments, the other camera determines and reports location and orientation information for the coordinate frame of each such instrument in a reference frame, such as the stereoscopic camera 106. Then, using linear algebra, the poses and/or locations of instruments relative to each other are calculated by the processor 1102 and/or the robotic arm controller 1106, thereby resulting in a calibration of the camera 106 to the robot space.

In some embodiments, the processor 1102 and/or the robotic arm controller 1106 are also configured to calibrate for the coupling plate 306. In some instances, the coupling plate 306 includes one or more switches that activate depending on a position of joints R7 to R9. The known position of the switches is used by the processor 1102 and/or the robotic arm controller 1106 as part of the coordinate transformation. Additionally or alternatively, the coupling plate 306 is calibrated by causing the robotic arm 114 to move while images from the camera 106 are monitored to determine orientation. In an example where the coupling plate 306 is orientated as shown in FIG. 10, the robotic arm 114 is commanded to move in a direction relative to an assumed orientation (for example, moving the camera 106 along the z-axis). If the assumed orientation is as shown in FIG. 10, wherein the camera 106 is aimed downward, a downward movement of the robotic arm 114 should cause an object in the image to get larger as the camera 106 gets closer. If, for example, the object in the image, instead moves sideways or up/down, then the processor 1102 and/or the robotic arm controller 1106 are configured to detect the motion and determine that the assumed orientation is incorrect. The processor 1102 and/or the robotic arm controller 1106 may generate an error and prompt an operator for the correct orientation and/or determine the correct orientation based on the detected movement in the images. The change in the image from movement of the camera 106 is deciphered automatically through use of, for example, image matching template algorithms, as described previously. In some embodiments, the use of matching template algorithms by the processor 1102 and/or the robotic arm controller 1106 determines joint orientation at the coupling plate 306, which is stored to a LUT for calibration.

Figure 13:
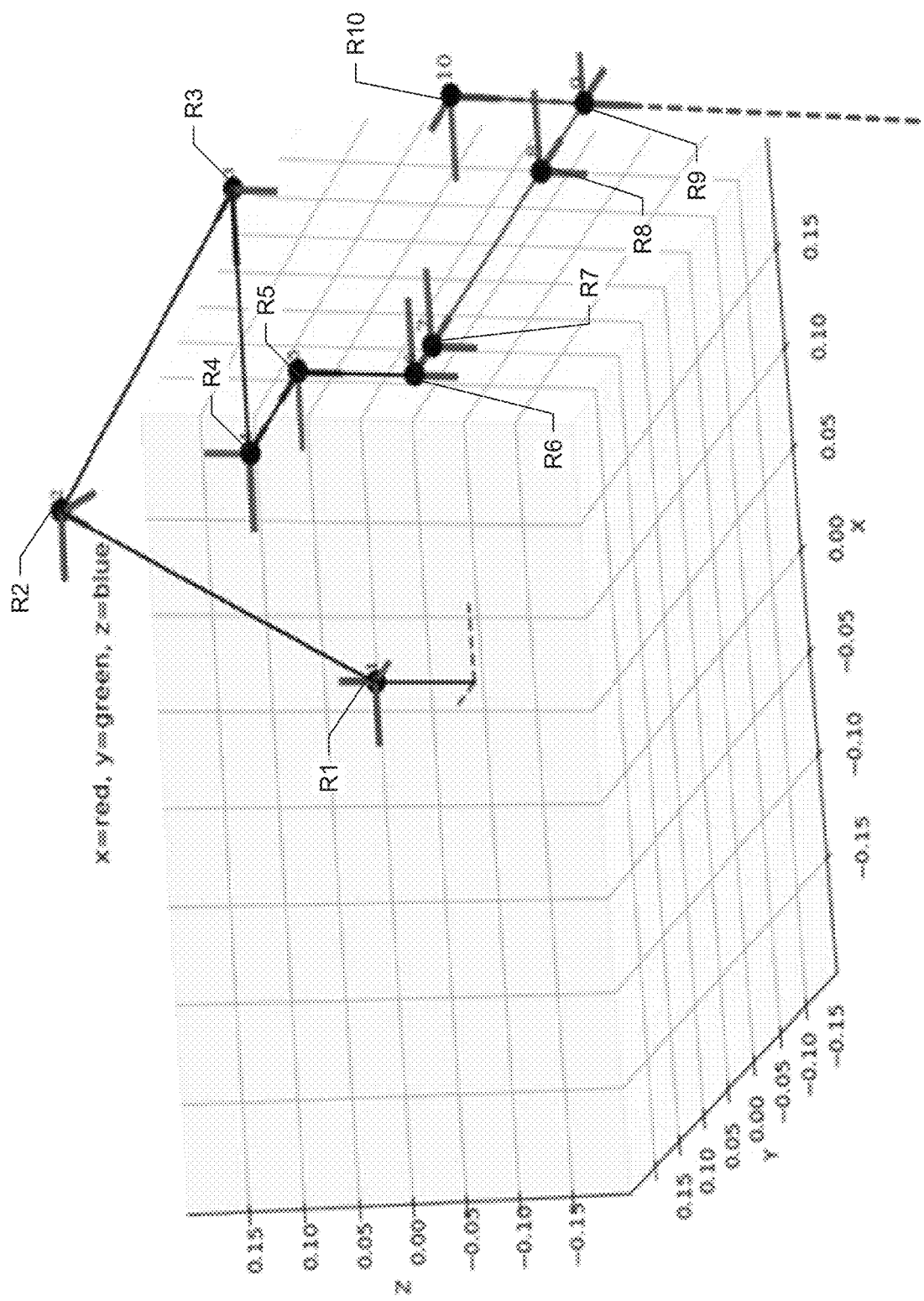
FIG. 13 shows a diagram that is illustrative of how the stereoscopic visualization camera and/or the robotic arm are calibrated to robot space, according to an example embodiment of the present disclosure.

FIG. 13 shows a diagram that is illustrative of how the stereoscopic visualization camera 106 and/or the robotic arm 114 are calibrated to robot space, according to an example embodiment of the present disclosure. In the illustrated embodiment, each of joints R1 to R9 and corresponding links are modeled based on rotational capabilities and/or lengths. The memory 1120 may store the mathematical parameters associated with the model. Further, the processor 1102 and/or the robotic arm controller 1106 may use the mathematical model to determine, for example, a current position of the robotic arm 114 and/or camera 106, which may be used for calculating how joints are to be rotated based on intended movement provided by an operator.

In the illustrated example, joint R1 is provided at a coordinate position of (0,0,0). The lengths between the joints R1 to R9 correspond to a length of the links. In the illustrated example, the stereoscopic visualization camera 106 is modeled as a robot end effector that is connected to nine couplers. The three-dimensional space shown in FIG. 13 is modeled using a sequence of ten homogeneous transformations, which may include matrix multiplications. The first six frames or joints R1 to R6 represent the forward kinematics of the robotic arm 114, and may be calculated using the Denavit-Hartenberg parameters of a robotic arm. The next three frames or joints R7 to R9 represent the transform from the tool-tip of the robotic arm 114 to a tip of the coupling plate 306. The last frame R10 represents the transform from the tool-tip of the coupling plate 306 to the control point of the stereoscopic visualization camera 106.

Frame or joint R7 represents the pitch joint of the coupling plate 306, which, can change between 0° and 90°. Frame or joint R8 represents the yaw joint of the coupling plate 306, and can change between −90°, 0°, and 90°, depending on the yaw configuration. Joints R7 to R9 of the coupling plate may include a voltage source and a potentiometer. The connector 3450 and/or the coupler controller 1130 of the robotic arm 114 may include an I/O tool-tip connector that is configured to receive a voltage output from the potentiometer. The processor 1102 and/or the robotic arm controller 1106 are configured to receive the output voltage and correspondingly determine pitch and yaw angles of the coupling plate 306. The processor 1102 and/or the robotic arm controller 1106 combines the pitch and yaw information of the coupling plate with sensor output data from joints R1 to R6 of the robotic arm 114 to calculate position of the frames R1 to R10 to determine the three-dimensional position of the robotic arm 114, the coupling plate 306, and/or the camera 106.

The control point represents frame 10 at the very end of the kinematic chain, and is fully programmable in terms of position based on which feature is selected. For example, if an operator selects an assisted drive feature, the processor 1102 and/or the robotic arm controller 1106 are configured to set the control point representative of the camera 106 to be inside of the camera along an axis of rotation of the control arms 304. In another example, if an operator selects a lock-to-target feature, the processor 1102 and/or the robotic arm controller 1106 are configured to set the control point of the camera 106 to an origin of an optical axis view vector.

Returning to FIG. 12, after calibrating the camera 106 to robot space, the processor 1102 and/or the robotic arm controller 1106 are configured to calibrate the robot space to patient space (block 1208). Calibration of patient space is need to enable the stereoscopic robotic platform 302 to make accurate visualizations of a patient, where the orientation between robot system and patient is needed. In some embodiments this orientation is fixed. In other embodiments the orientation, if varying, is sensed and known. In some embodiments a patient is placed in an operating room bed and registered to the bed using one or more fiducials 1209. For example, if a patient is undergoing brain surgery, they are secured to a bed and an external frame is fixed to their skull. The frame is observable by the stereoscopic visualization camera 106 and may comprise fiducials 4809 in an arrangement such as that of the calibration target where two or more non-collinear objects of known locations are visible simultaneously, such that the position and orientation of the frame, and hence the patient's skull, is capable of being determined. Other embodiments may use fiducials 4809 that are implanted into a patient and are visible in MRI or similar images. Such fiducials 4809 can be used to accurately track and register a patient's skull as well as the MRI image to a coordinate system representative of patient space. Further, other embodiments may use image recognition of features native to the patient themselves. For example, facial or similar recognition using biometric data, in-situ x-ray, or similar alternative modality imaging can be used to precisely locate a position and orientation of the patient. In another example, a model of a surface of a patient's face can be determined using one or more depth map calculations as described above, and surface matching functions performed by the processor 1102 and/or the robotic arm controller 1106.

In an embodiment, a position and orientation of an operating room bed with respect to robot space is fixed and determined. Some embodiments comprise a rigid frame which mechanically registers the bed to, for example, fittings on the cart 120 in a known position and orientation. Alternatively, the bed can be fixed with respect to the robotic arm 114 and fiducials can be used to determine position and orientation. For example, the robotic cart 120 and bed can be anchored to the floor and fixed for the duration of the procedure.

After visualization of the patient's fiducials 1209 by the camera 106, their position and orientation in robot space can be deciphered and stored by the processor 1102 and/or the robotic arm controller 1106, where coordinate system transformations from robot space to patient space are enabled. It is noted that coordinate system transformations from one space to another are generally selectable and reversible. For example, it may be more efficient to transform desired camera motions or poses into robot space to enable the processor 1102 and/or the robotic arm controller 1106 to determine discrete joint motion and orientation. Alternatively, it may be easier and more efficient to present information to a surgeon on the display monitor 512 in patient space. Location of points and vectors can be transformed by the processor 1102 and/or the robotic arm controller 1106 to be respective of most any coordinate system, for example, a cart origin, a patient reference frame, GPS, and/or other coordinate systems as desired.

In some embodiments, the processor 1102 and/or the robotic arm controller 1106 are configured to use automated, iterative techniques to perform these or equivalent methods of robot/patient space calibration and measurement to increase accuracy and reduce calibration time. In exemplary embodiments, the displacement and orientation of the stereoscopic visualization camera 106 with respect to fiducials is accurately known by the processor 1102 and/or the robotic arm controller 1106. Motion of the robotic arm 114 can be accurately performed, and the subsequent images of fiducials can be accurately analyzed. The visualization and knowledge of the calibration parameters can be combined by the processor 1102 and/or the robotic arm controller 1106 such that measurement, and hence calibration can be accurately performed in an automated manner. This is important, for example, to maintain accurate calibrations from one surgical procedure and one patient to the next.

In some examples, the processor 1102 and/or the robotic arm controller 1106 are configured to determine boundaries of the robotic arm 114 and/or camera 106 relative to the patient space and/or robot space (block 1210). The boundaries represent virtual limits that are implemented in the software to prevent the robotic arm 114 and/or the camera 106 from contacting or escaping defined areas or spaces. In some examples, the limits are defined in one or more LUTs or registers stored in the memory 1120 as scale factors that are applied to joint movement signals by the processor 1102 and/or the robotic arm controller 1106. The magnitude of the scale factor is decreased to zero as the limit to each individual boundary is approached. For example, the joint rotation amount and speed may be determined based on operator input. However, the processor 1102 and/or the robotic arm controller 1106 scales the joint rotation speed by the scale factor before sending the signal(s) to the appropriate joint(s). In addition, the processor 1102 and/or the robotic arm controller 1106 may maintain the rotation amount such that the joint moves the desired amount, but at a reduced speed, until the joint reaches the boundary. It should be appreciated that a joint in a rotation area where a scale factor is applied may not have a scale factor applied if the desired movement is away from the boundary. Thus, the processor 1102 and/or the robotic arm controller 1106 may apply a scale factor to certain joints while applying a scale factor of '1' to other joints based on a current position and estimated desired movement from an operator.

The scale factors are strictly between zero and one, which enables chaining them together and enables the software to support an infinite number of possible boundaries. The scale factors may be lineally decreased as a boundary is approached, which causes a gradually slowing of the rotation of joints R1 to R9 as the robotic arm 114 approaches a boundary. In other examples, the scale factors may decrease exponentially as a boundary is approached.

In addition to the boundaries for the robotic arm 114, the memory 1120 may store boundaries that relate to Cartesian limits that prevent the robotic arm 114 from hitting the cart 120, the robotic arm from hitting the display monitor 512, and/or the camera 106 from hitting the robotic arm 114. The processor 1102 and/or the robotic arm controller 1106 may use, for example, the coordinate system discussed in conjunction with FIG. 13 for determining and/or applying the Cartesian limits. In some examples, the limits may be relative or anchored to a certain link. As such, when the link is moved in the 3D space, the boundary around it moves accordingly. In other examples, the limits are static and fixed to certain coordinate planes or lines within the 3D space shown in FIG. 13. The processor 1102 and/or the robotic arm controller 1106 may apply the limits by calculating or determining scale factors in Cartesian space and applying the forward kinematic transform.

The example processor 1102 and/or the robotic arm controller 1106 may also determine a patient boundary, which defines a virtual place that no point of the robotic arm 114 and/or camera 106 can violate. Patient boundaries may be determined by calculating scale factors in Cartesian space for a distance of each positional joint on the robotic arm 114 and/or the coupling plate 306 to a location of a boundary plane. The example boundaries may be stored to the memory 1120 as default boundaries and/or determined by the processor 1102 and/or the robotic arm controller 1106 prior to a surgical procedure. In some embodiments, certain boundaries may be accessed or determined based on an inputted type of surgical procedure to be performed. For example, patient boundaries may be determined by the camera 106 imaging the patient and determining patient depth using calibration information/parameters. The processor 1102 and/or the robotic arm controller 1106 may then create and apply a boundary to a specified location above or next to the patient. Similar boundaries may be created after detection of monitors, surgical staff, or surgical instruments.

1. Sag Compensation Embodiment

In some embodiments, at least some of joints R1 to R9 of the robotic arm 114 and/or the coupling plate 306 may experience some sag. The processor 1102 and/or the robotic arm controller 1106 may be configured to provide correction for robotic arm sag. In some instances, the processor 1102 and/or the robotic arm controller 1106 are configured to perform sag compensation on a series of small moves, such that motion accuracy is preserved over a range of motion of the robotic arm 114. For example, to characterize and eliminate sag, sag compensation is performed in motion directions that exercise a particular robotic joint to isolate error as a function of actual robot joint rotational position. By comparing the error to torque moments calculated by multiplying camera 106 load weight by moment arm (or link) length, the compliance of that joint can be determined. Alternatively, joint compliance may be calculated using analytical techniques, for example Finite Element Analysis ("FEA").

Using and storing the above-compliance characterization for all the joints in all rotational positions, the processor 1102 and/or the robotic arm controller 1106 may calculate the overall sag for a particular camera position. The processor 1102 and/or the robotic arm controller 1106 may determine a sag correction factor for each camera position to a LUT and/or calibration registers. Further, the processor 1102 and/or the robotic arm controller 1106 may apply the sag correction factor to robotic arm move commands or a movement sequence (before or after scale factors are applied) such that sag compensation is incorporated into movement commands/signals. The correction factor may be calculated in an ongoing motion procedure, thereby enabling accurate tracking and following of the camera 106. This correction factor further eliminates a need for a second camera for calibration/positioning of the stereoscopic robotic platform 302, and eliminates the need to have fiducial targets on the camera 106, and hence eliminates a problem of drape interference.

D. Assisted Drive Embodiments

In some embodiments, the processor 1102 and/or the robotic arm controller 1106 are configured to execute one or more algorithms, routines, etc. defined by instructions stored in the memory 1150 and/or 1120 to enable the robotic arm 114 and/or the coupling plate 306 to provide powered joint movement based on detected forces applied by an operator for moving the stereoscopic visualization camera 106 (block 1212). In these embodiments, the assisted drive feature enables the robotic arm 114 to operate as an extension of a surgeon by moving the stereoscopic visualization camera 106 to a desired location and/or orientation. For example, the processor 1102 and/or the robotic arm controller 1106 are configured to monitor force/torque/movement imparted by an operator and positions of arm joints to infer an operator's intent and accordingly move the robotic arm 114 and/or the coupling plate 306.

III. Calibration of Force/Torque Sensor

Systems and methods for calibrating the force/torque sensor (e.g., sensor 115 of FIGS. 1-3, 5, and 11) across multiple dimensions in real-time are thus described. At least one method analytically characterizes most or all dimensions of non-linearity and cross-coupling through a quick calibration, resulting in performance improvements that enable high performance applications to be accomplished force-torque sensors using minimal computing resources and little to no training.

A. Linearity Analysis

In at least one embodiment, calibration of the force/torque sensor 115 may begin with the determination of the linearity of the force/torque sensor 115. To analyze the linearity behavior of the sensor 115, two tests may be performed.

Figure 14:
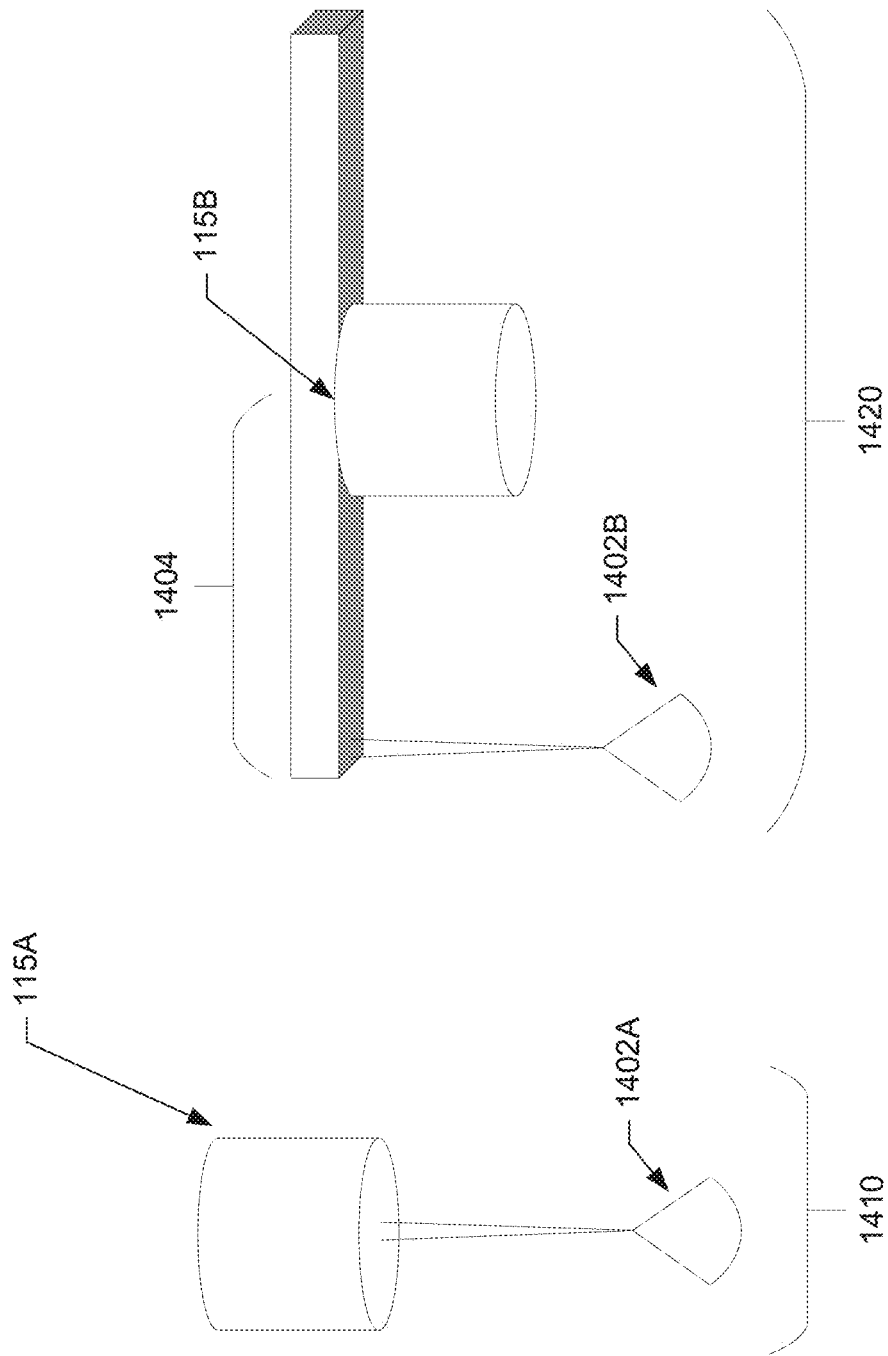
FIG. 14 is a drawing illustrating two tests for determining the linearity behavior of the sensor, in accordance with an example embodiment of the present disclosure.

FIG. 14 is a drawing illustrating two tests for determining the linearity behavior of the sensor, in accordance with an example embodiment of the present disclosure. In the first test, as shown by marker 1410, a force may be applied incrementally to the origin (e.g., Cartesian center point) of the sensor 115A to minimize the amount of torque applied to the sensor. This test checks the linearity of the sensor independent of any torque. In the second test, as shown by marker 1420, a force may be applied off-center from the origin of the sensor to produce a torque. The force is off-center as it is applied a distance 1404 from the origin of the sensor. The aim of the second test is to consider the effect of the coupling on the sensor measurement. The second test may be performed by adding weights at the end-effector where the sensor 115B may be installed. In at least one embodiment, the sensors 115A-115B may comprise an E-series sensor, having a frequency of 500 Hz. The force measurement data may be collected by averaging every 50 samples with corresponding time stamp. The resultant frequency may be about 10 Hz.

Figure 15:
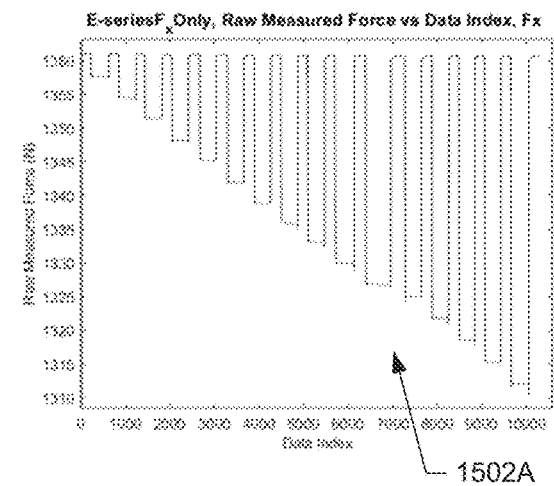
FIG. 15 is a collection of charts depicting the linearity test results based on the application of force at the origin of the sensor (e.g., the first test), in accordance with an example embodiment of the present disclosure.
Figure 15:
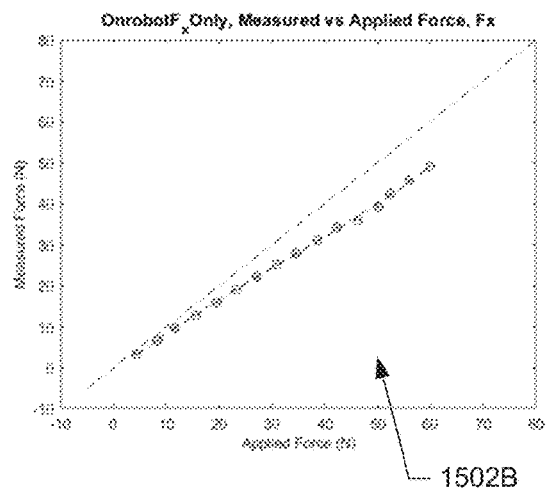
Figure 15:
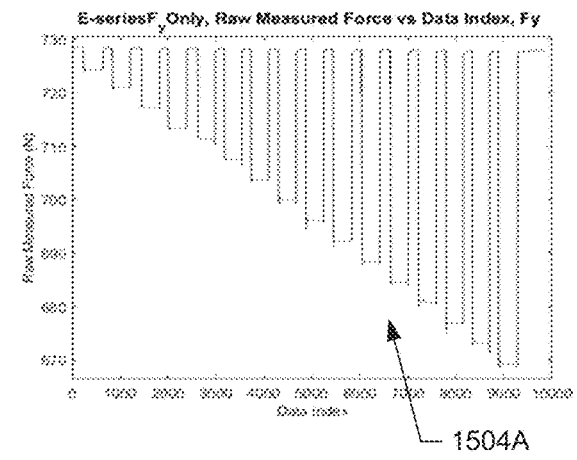
Figure 15:
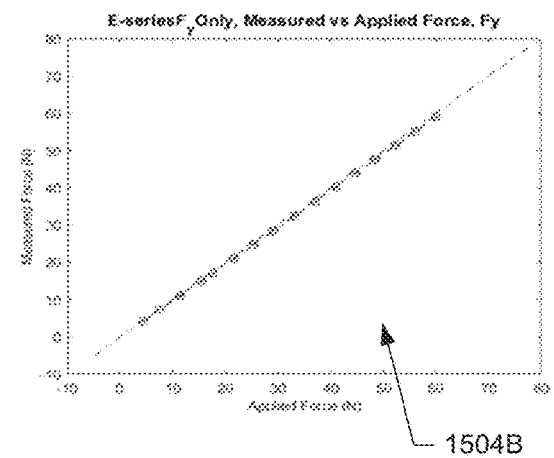
Figure 15:
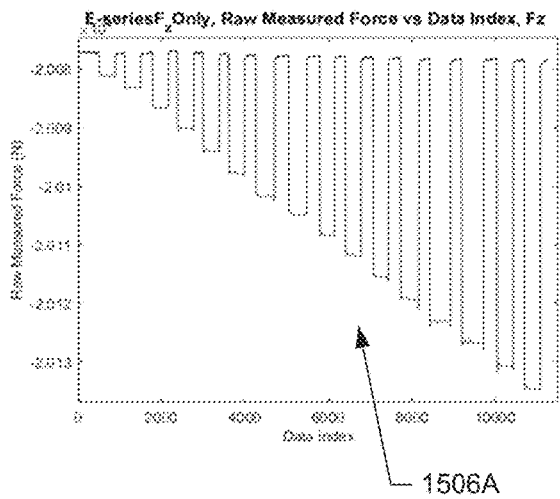
Figure 15:
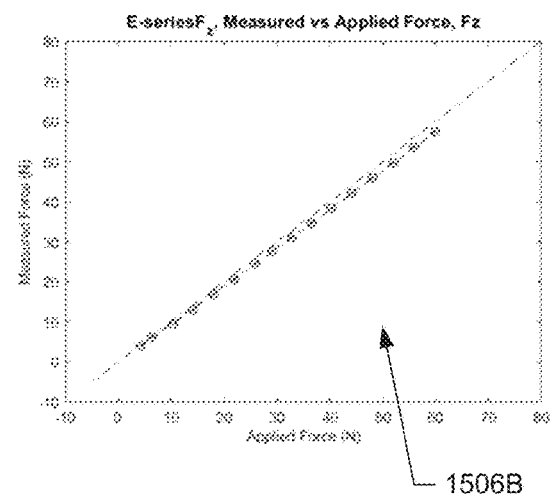

FIG. 15 is a collection of charts depicting the linearity test results based on the application of force at the origin of the sensor (e.g., the first test), in accordance with an example embodiment of the present disclosure. As demonstrated in charts 1152A, 1504A, and 1506A of FIG. 15, the region of interest is selected and averaged out to find a sensor measurement based on the applied forces. Charts 1152B, 1504B, and 1506B of FIG. 15, which corresponds to 1152A, 1504A, and 1506A of FIG. 15, show the sensor measurement (indicated by black circle) and show how the measurement is changing by increasing the weight. The dotted red line indicated the actual force value and is an indicator how the measurement is deviating from the path. The error bar in each circle shows how the measurement changing. As illustrated in FIG. 15, the sensor measurement in the Z and Y direction is almost linear. Although the measurement in the X direction looks slightly off from the actual data, the measurement almost follows a straight path.

Figure 16:
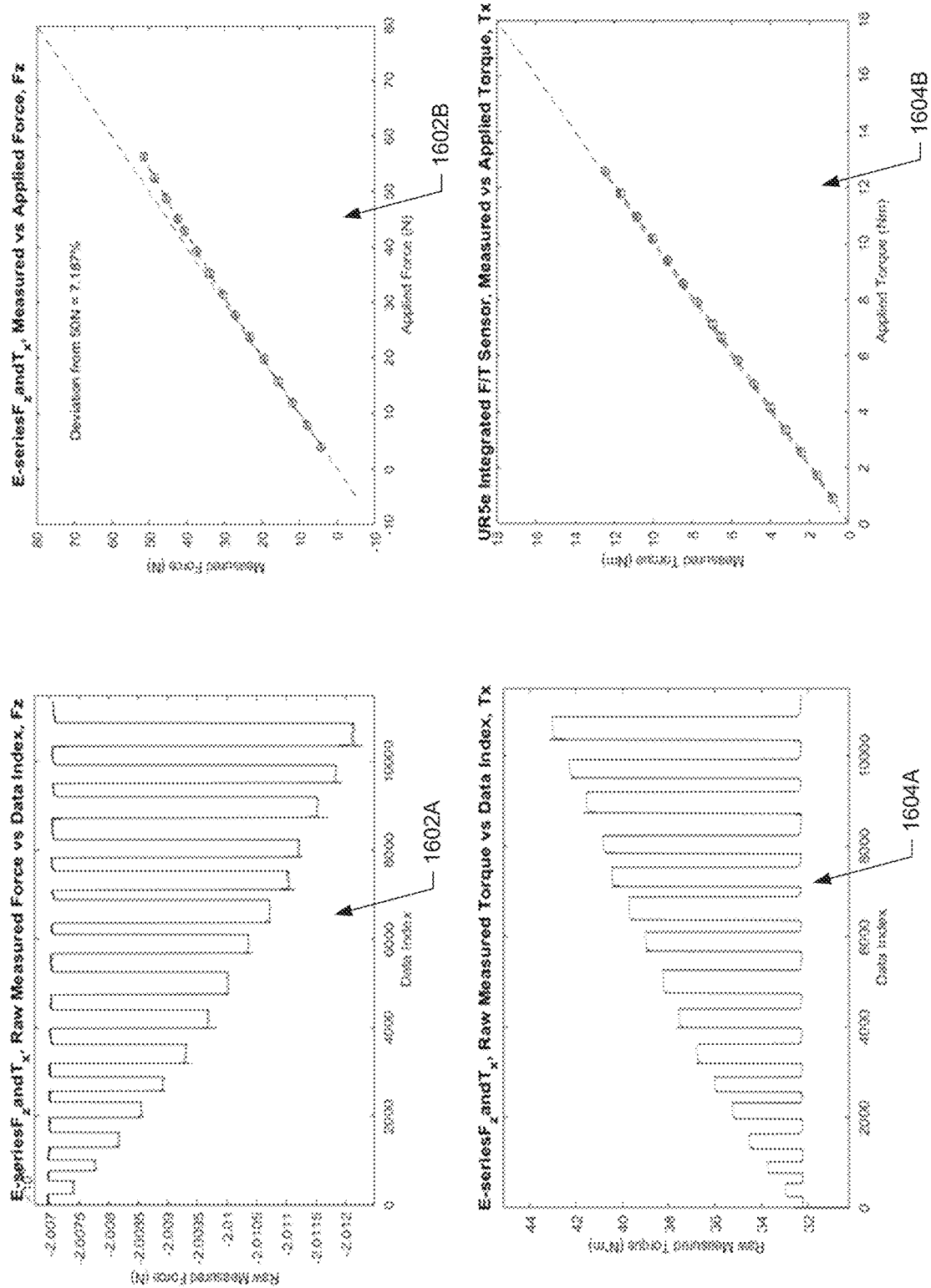
FIGS. 16-18 comprise a collection of charts depicting the linearity test results based on the application of force off-center from the origin of the sensor (e.g., the second test), in accordance with an example embodiment of the present disclosure.
Figure 17:
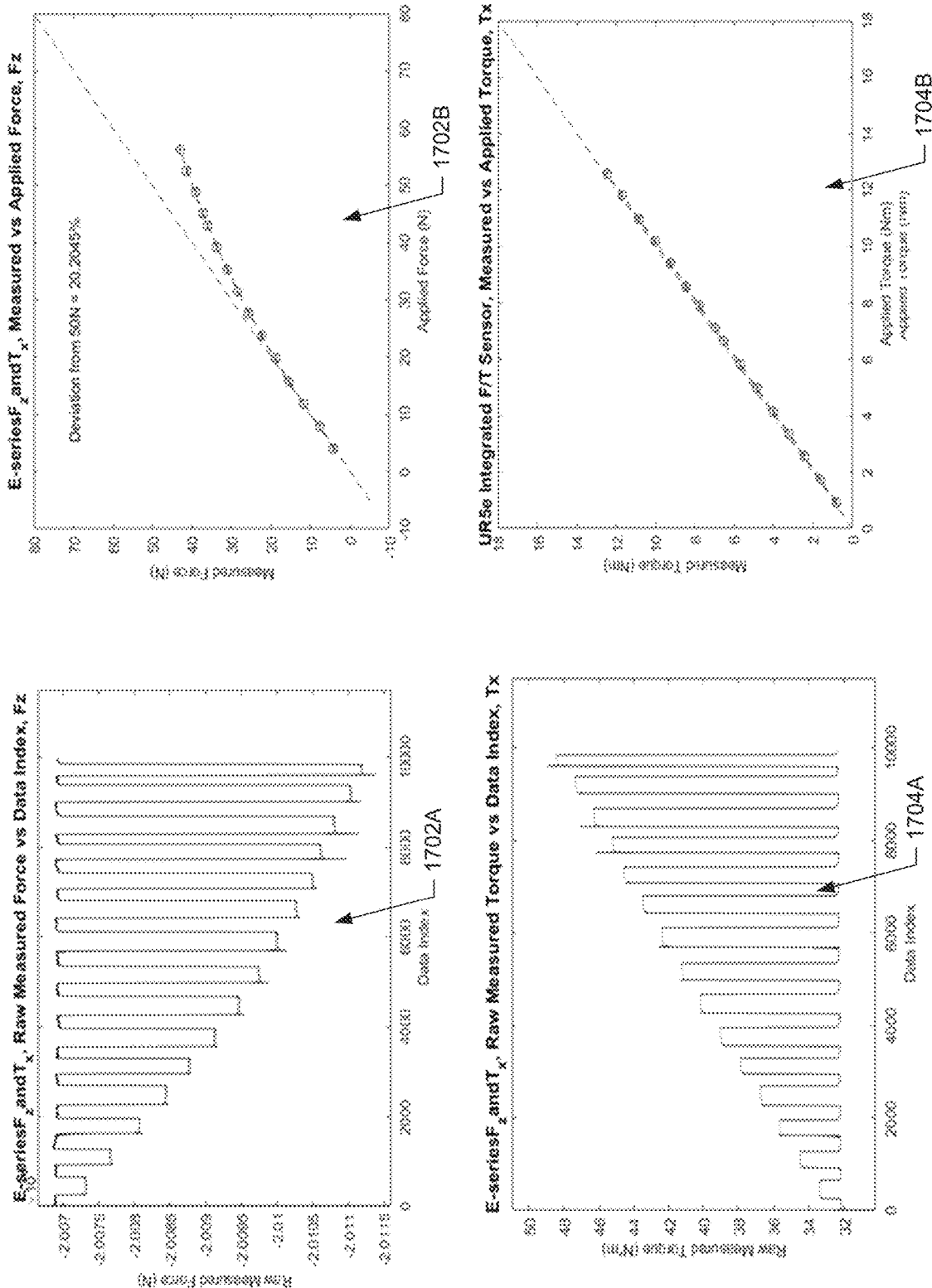
Figure 18:
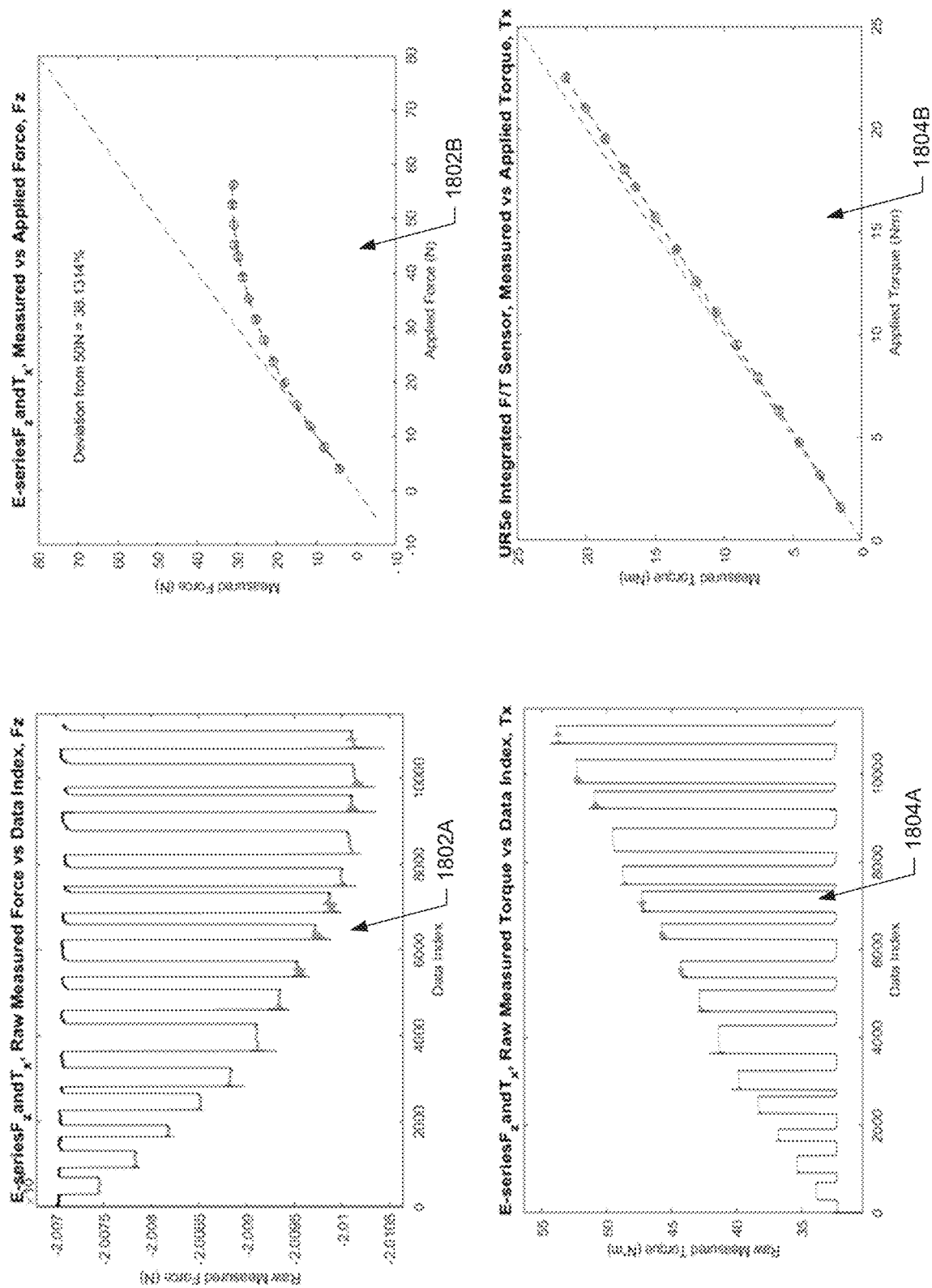

FIGS. 16-18 comprise a collection of charts depicting the linearity test results based on the application of force off-center from the origin of the sensor (e.g., the second test), in accordance with an example embodiment of the present disclosure. The second test is carried out by applying a force at three different distances away from the sensor's center frame. For example, referring back to FIG. 14, the force may be applied at three different distances by varying the distance 1404. Unlike the first test shown in FIG. 15, the second test whose results are shown in FIGS. 16-18 evaluates the coupling effect between the sensor measuring the force and the corresponding sensor that measures the torque. The results for the second test are shown in charts of FIGS. 16-18. For example, FIG. 16 indicates the measured torque versus the applied torque as force is applied 20 centimeters away from the center of sensor 115B, FIG. 17 indicates the measured torque versus the applied torque as force is applied 30 centimeters away from the center of sensor 115B, and FIG. 18 indicates the measured torque versus the applied torque as force is applied 40 centimeters away from the center of sensor 115B. The measurements illustrated in FIGS. 16-18 indicate that the nonlinearity of measurement in Z-direction has a relation with moment arm. As the moment arm increases, the nonlinearity increases too.

Figure 19:
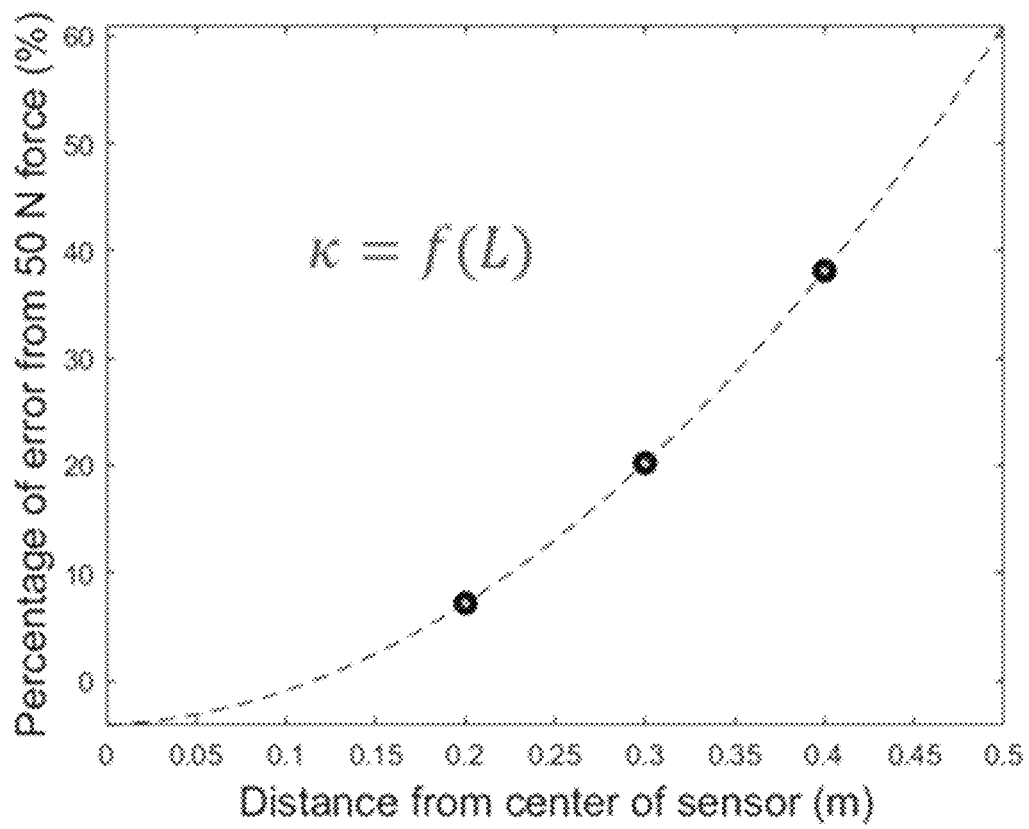
FIG. 19 is a graph illustrating the effect of moment arm on the nonlinearity of the sensor in the Z-direction, in accordance with a non-limiting embodiment of the present disclosure.

FIG. 19 is a graph illustrating the effect of moment arm on the nonlinearity of the sensor in the Z-direction, in accordance with a non-limiting embodiment of the present disclosure. FIG. 19 shows how the torque reading of the torque/force sensor (e.g., sensor 115B of FIG. 15) deviates from the desired reading. In the example chart shown in FIG. 19, the error is measured for an applied force of 50N, and the error is indicated as percentage that the reading has diverged from the expected reading. The example results obtained from the torque measurement about the X-axis for a given sensor (e.g., the E-series force/torque sensor) show a good linearity behavior under the applied forces. For example, according to the UR specification sheet for the E-series Force/Torque sensor, the limit for the torque is 10 Nm; the results shown in FIG. 19 indicate that exceeding the limit to some extent (e.g., over 20 Nm) does not introduce nonlinearity on the sensor reading.

B. Correction Parameters

Various embodiments for determining the corrections parameters in real time are described. In at least one embodiment, correction parameters may be determined via a polynomial equation, based on the results of the linearity analysis discussed above. For example, the polynomial equation may be represented as:

$F_c = q_1(F_m - F_0) + q_2(F_m - F_0)(F_m - F_0)$, where $F_c$ is a polynomial function for the correction of force being applied at a location (e.g., an origin) of the sensor, $q_1$ and $q_2$ are the correction parameters, and $F_m - F_0$ is a difference between the measured force being applied at the location and the sensor's baseline for the forces.

However, as previously discussed in relation to FIG. 19, the nonlinear curve of the percentage of error in the measurement of a force by the force/torque sensor may be a function of moment arm (e.g., a distance from center of sensor). Thus, to generalize the equation, a term L signifying the moment arm may be added to the equation (1):

$$F_c = q_1(F_m - F_0) + q_2(F_m - F_0)(F_m - F_0)L(T_m - T_0) \tag{1}$$

which results in $$F_c = q_1(F_m - F_0) + q_2(F_m - F_0)(T_m - T_0) \tag{2}$$

Similarly, since torque was previously shown to have almost linear behavior independent from the other coordinates, the polynomial equation for torque may be represented as:

$$T_c = b_1(T_m - T_0) + b_2(T_m - T_0)^2, \tag{3}$$

where $T_c$ is a polynomial function for the correction of torque being applied at a location (e.g., moment arm), $b_1$ and $b_2$ are the correction parameters for the measured torque, and $T_m - T_0$ is the difference between the measured torque being applied at the location and sensor's baseline for the torque.

Since equation (2) depends on the torques, and the torques values will be updated using the equation (3), we need to pass the updated torque value into the equation (4). Therefore, $$F_c = q_1(F_m - F_0) + q_2(F_m - F_0)T_c \tag{4}$$

In order to solve these equations analytically, the equation may be written in a matrix format:

$$F_c = [p_0 \ p_1 \ p_2 \ p_3] \begin{bmatrix} 1 \\ F_m \\ T_c \\ F_m * T_c \end{bmatrix} \tag{5}$$

where $p_0 = -q_1 F_0$, $p_1 = q_1$, $p_2 = -q_2 F_0$, and $p_3 = q_2$.

For reasons discussed below, the matrix $[p_0 \ p_1 \ p_2 \ p_3]$, is referred to as P, and the matrix $$\begin{bmatrix} 1 \\ F_m \\ T_c \\ F_m * T_c \end{bmatrix}$$

is referred to as $S_F$.

Likewise the torque equation can be written as $$T_c = \begin{bmatrix} a_0 & a_1 & a_2 \end{bmatrix} \begin{bmatrix} 1 \\ T_m \\ T_m^2 \end{bmatrix} \quad (6)$$

where $a_0 = b_2 T_0^2 - b_1 T_0$, $a_1 = b_1 - 2b_2 T_0$, and $a_2 = b_2$.

For reasons discussed below, the matrix $[a_0 \; a_1 \; a_2]$ is referred to as A and the matrix $$\begin{bmatrix} 1 \\ T_m \\ T_m^2 \end{bmatrix}$$

is referred to as $S_T$.

In order to find the correction parameters, a set of input and outputs can be generated as a training data. The input of the system may comprise the sensor readings (e.g., of force and torque), and the output may comprise the forces and torques under the gravity effect calculated based on the end-effector mass and center of mass.

Figure 20:
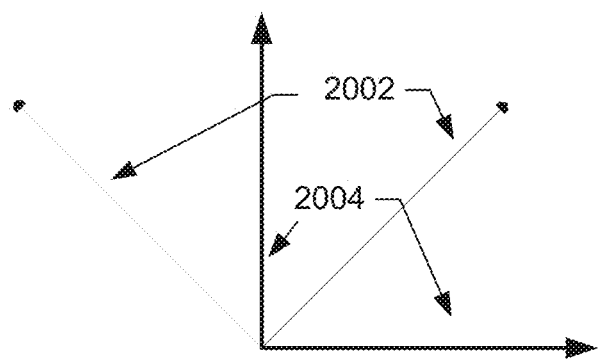
FIG. 20 is an illustration showing an example coordinate frame of the force/torque sensor juxtaposed with the coordinate frame of gravity, in accordance with a non-limiting embodiment of the present disclosure.

FIG. 20 is an illustration showing an example coordinate frame of the force/torque sensor juxtaposed with the coordinate frame of gravity. As shown in FIG. 20, the coordinate frame of the force/torque sensor ("sensor coordinate frame") 2002 may not necessarily be the same as the coordinate frame of gravity ("gravity coordinate frame") 2004.

After collecting all the data, the equation (7) and (8) are used to find the correction parameters.

$$P = F_g F_s^+ \quad (7)$$

$$A = T_g S_T^+ \quad (8)$$

where $F_g$ and $T_g$ are forces and torques under the gravity effect respectively, and where $S_F$ and $S_T$ are the matrices for force and torque, respectively, under the sensor coordinate frame, as previously mentioned in relation to equations (5) and (6). Furthermore, P and A are the matrices for the correction parameters for force and torque, also as previously mentioned in relation to equations (5) and (6). The superscript (+) is the convention to indicate pseudoinverse.

Figure 21:
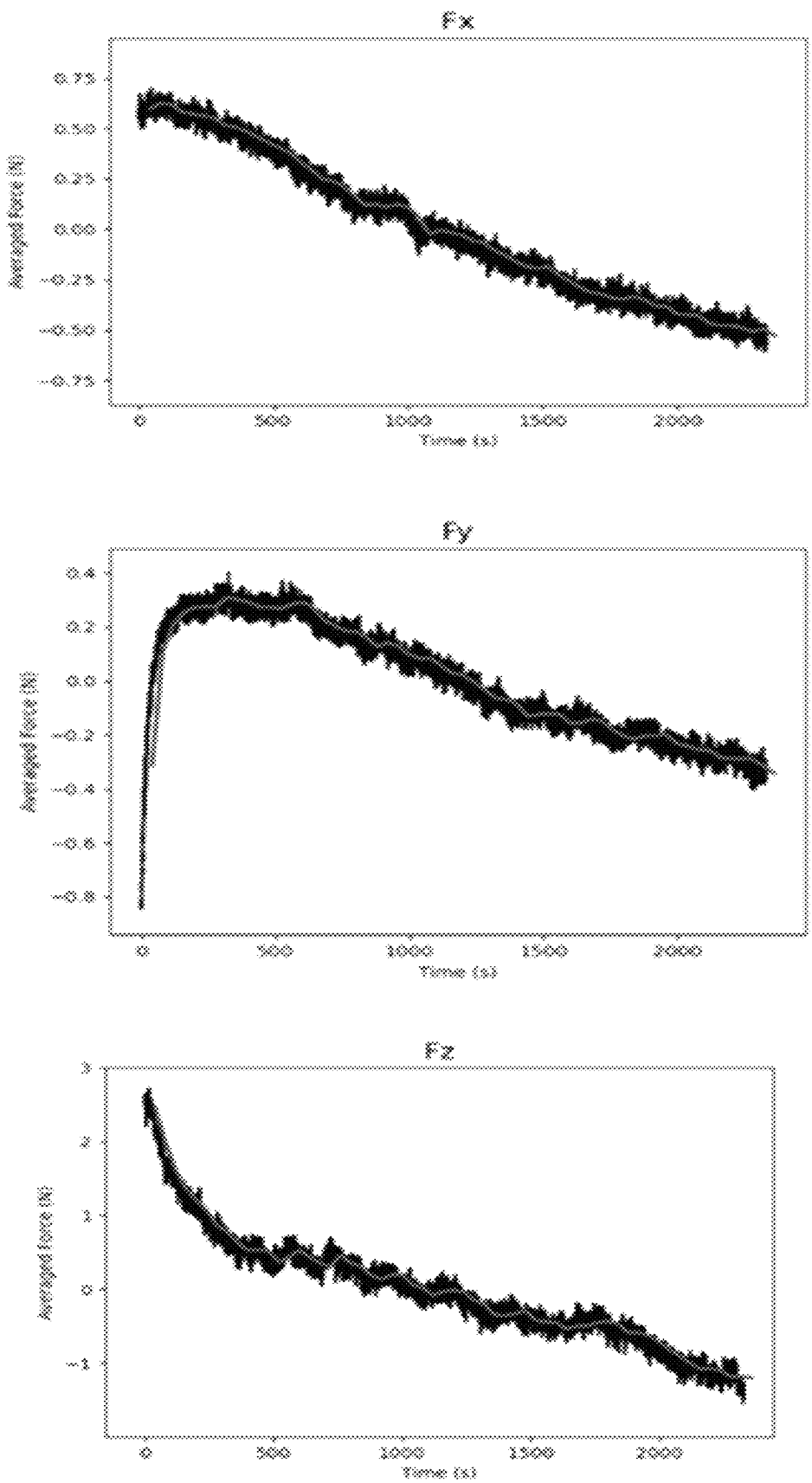
FIG. 21 includes graphs showing a drifting of the baseline measurement of force of a sensor, in accordance with an example embodiment of the present disclosure.

In order for the previously discussed correction parameters to be functional, the sensor's base line may need to be fixed such that the base line does not change over time. For example, as shown in FIG. 21, experimental results have shown that the sensor's baseline can drift over time. Also, it has been observed that the sensor's baselines can be slightly different each time a force/torque sensor turns on or turns off. Therefore, various systems and methods for updating the correction parameters are described, e.g., to account for any drifting of a sensor's baseline.

In at least one embodiment, the polynomial equations (4) and (3) which has the clear offset parameters that can be updated mathematically. In order to do so, the correction parameters found from equations (5) and (6) can be mapped to the one from equations (4) and (3) respectively.

In order to have a one-to-one map from p→q, a new parameter can be added to equation (2), to result in:

$$F_c = q_1(F_m - F_0) + q_2(F_m - F_0)T_c + q_3 T_c \quad (9)$$

where the correction parameters can be obtained as below $$F_0 = -\frac{p_0}{p_1} \quad (10)$$

$$q_1 = p_1$$

$$q_2 = p_3$$

$$q_3 = p_2 - p_3 \frac{p_0}{p_1}$$

Similarly, a one-to-one mapping from a→b can be calculated using the following equations:

$$T_0 = \left\{ -s_1 + \frac{\sqrt{s_1^2 - 4s_0 s_2}}{2s_0}, -s_1 - \frac{\sqrt{s_1^2 - 4s_0 s_2}}{2s_0} \right\} \quad (11)$$

where $s_0 = 1$ $s_1 = \dfrac{a_1}{a_2}$ $s_2 = \dfrac{a_0}{a_2}$

Since two solutions can exist for $T_0$ based on equation (11), the correct solution may be the closest one to the measured sensor reading. Therefore, the $b_1$ and $b_2$ can be found from equations below $$b_1 = a_1 + 2a_2 T_0 \quad (12)$$

$$b_2 = a_2$$

The parameters can be separated out cleanly from the offset parameters. In at least one embodiment, the offset values can be calculated or recalculated mathematically when the sensor data is not being used by the robot (e.g., the robot is not in use). Furthermore, the calculated or recalculated offset parameter can then be applied to correct the measured forces or torques while the robot is in use.

$F_0$ can be found from equation (9), and $T_0$ can be found from equation (3) as follows:

$$F_0 = f(F_g, F_m, T_c, q_1, q_2, q_3) \quad (13)$$

$$T_0 = f(T_g, T_m, b_1, b_2) \quad (14)$$

Thus, the above methodology can allow the correction equation to remain true (e.g., valid), regardless of the sensor baseline.

C. Results and Discussion

Figure 22:
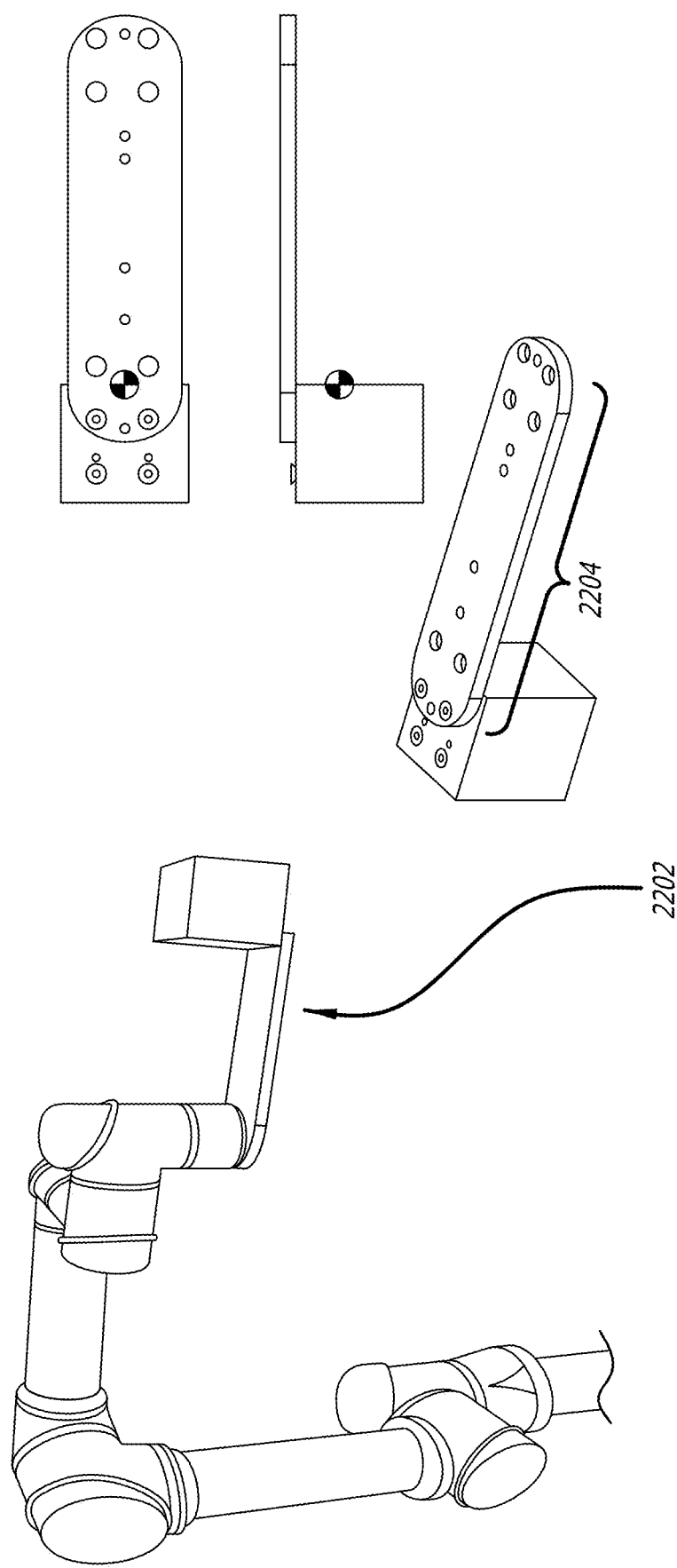
FIG. 22 is an illustration of a dummy end-effector for testing sensor correction, in accordance with an example embodiment of the present disclosure.

FIG. 22 is an illustration of a dummy end-effector for testing sensor correction, in accordance with an example embodiment of the present disclosure. To test the previously described sensor correction parameters, a dummy end-effector 2202 shown in FIG. 22 can be used. As shown in FIG. 22, the dummy end-effector 2202 has a moment arm 2204, which resemble our application. The weight of the end-effector is 4.8 kg and the center of mass is (0.208, 35) mm from the built-in force/torque sensor.

a. Training Data

Figure 23:
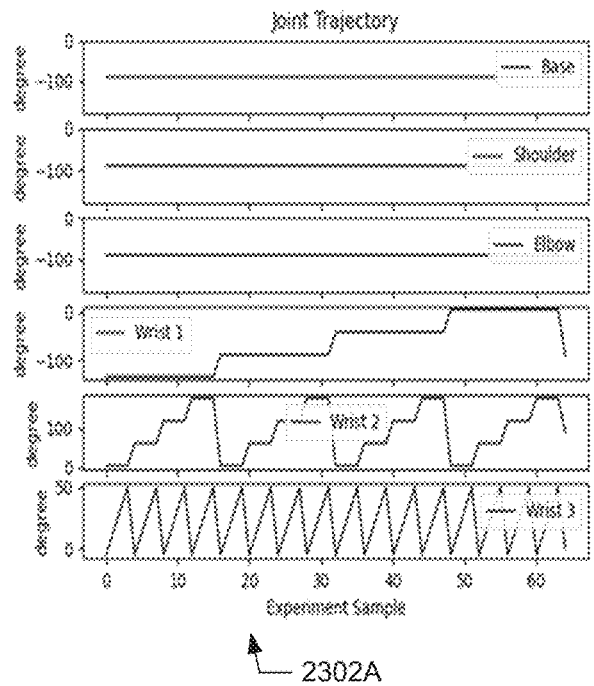
FIG. 23 includes graphs showing two example training data to be used to generate a correction model, in accordance with a non-limiting embodiment of the present disclosure.
Figure 23:
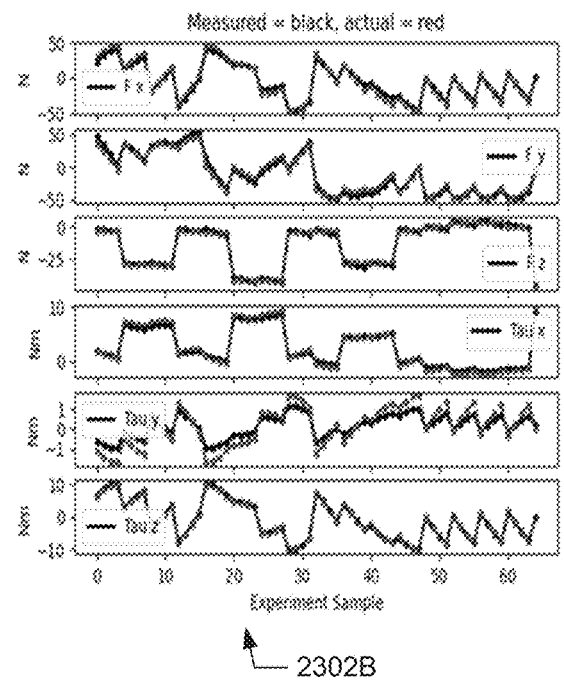
Figure 23:
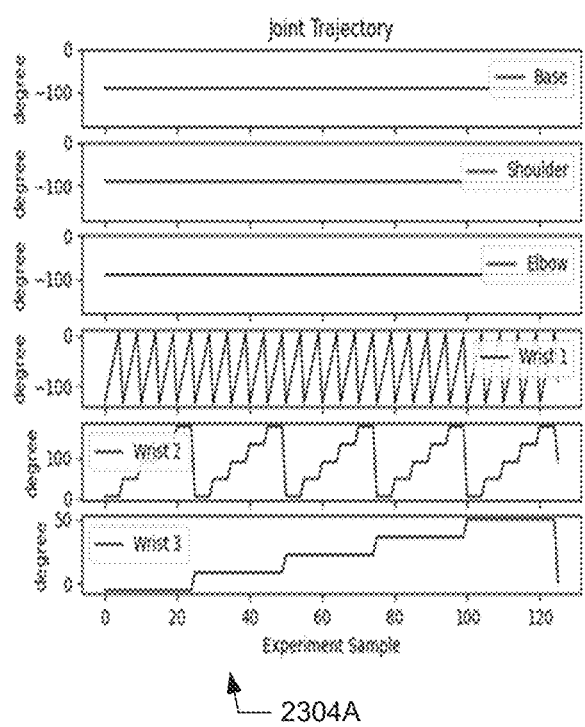
Figure 23:
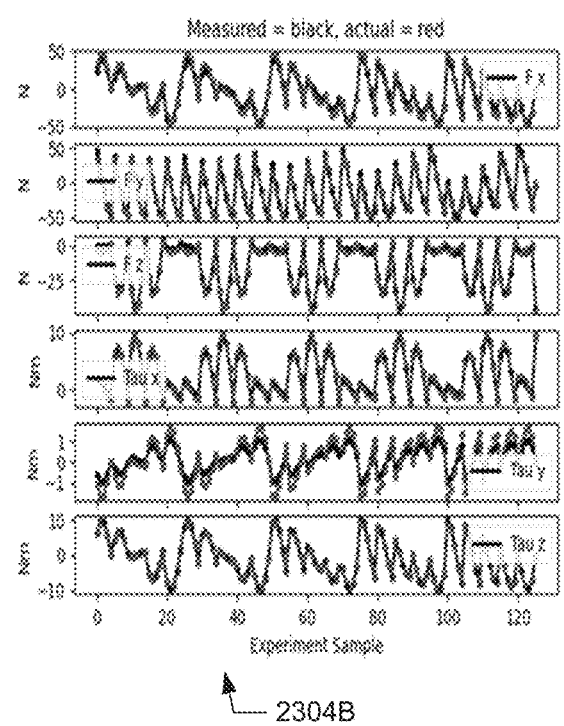

As previously discussed, a set of input and outputs can be generated as a training data. The input of the system may comprise the sensor readings (e.g., of force and torque), and the output may comprise the forces and torques under the gravity effect calculated based on the end-effector mass and center of mass. FIG. 23 includes graphs showing two example training data with 65 and 125 waypoints respectively. Specifically, graphs 2302a and 2302b shows example training data formed used 65 waypoints, and graphs 2304a and 2304b shows example training data formed using 125 waypoints. For each waypoint, 100 measurements may be obtained. As performed for the examples shown in FIG. 23, the average of the 100 measurements for a given waypoint can be computed as a measurement of that waypoint, and then the forces under the gravity values in sensor coordinate frame can be calculated. While graphs 2302a and 2304a show joint trajectories, graphs 2302b and 2304b show the corresponding data for sensor measurement versus gravity forces, respectively.

To subtract the baseline from the sensor reading, the difference between the sensor measurement and gravity values in each waypoint can be calculated. The average delta, $\Delta s$, of the difference for all sample measurements can thus be computed as follows:

$$\Delta s = \frac{\sum_{i=0}^{n} \text{sensor measurement}_i - \text{gravity}_i}{\text{Number of samples}} \quad (15)$$

Subsequently, the average delta, $\Delta s$, can be subtracted from sensor measurement as follows:

baseline subtracted sensor measurement$_i$=sensor measurement$_i$-$\Delta s$      (16)

b. Sensor Correction

Now, the training data can be used and plugged into equations (7) and (8) to find the first set of correction parameters. Once the parameters are determined, the parameters can be substituted into equations (10-12) to solve for equations (9), (3) and (13-14).

Figure 24:
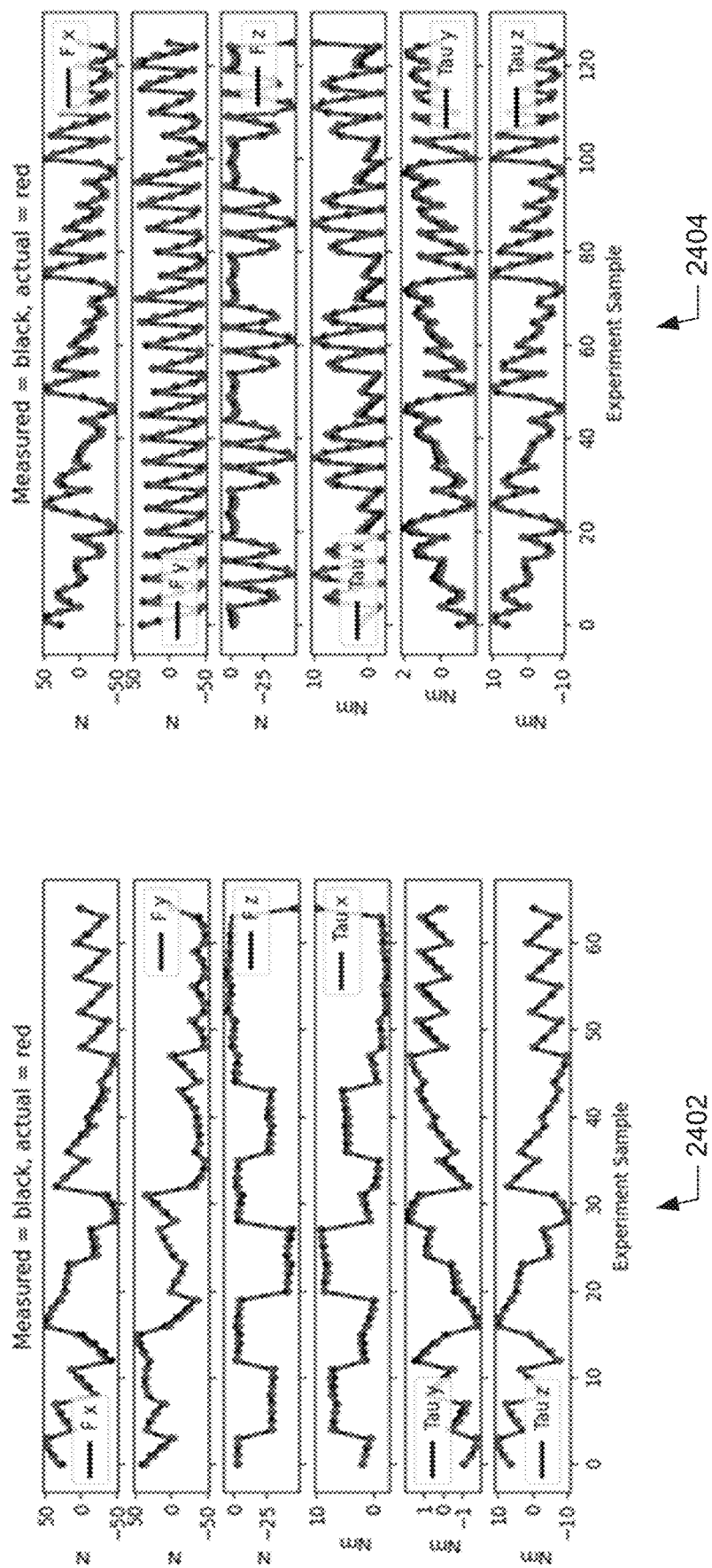
FIG. 24 includes charts showing forces and torque values after corrections have been applied, in accordance with an example embodiment of the present disclosure.

FIG. 24 includes charts showing forces and torque values after corrections have been applied, in accordance with an example embodiment. Specifically, chart 2402 shows the sample training data used in charts 2302a-2302b after the correction is applied. As shown in chart 2402, the averaged absolute forces improved by 41%, and the averaged absolute Torques improved by 56%. Chart 2402 shows the sample training data used in charts 2304a-2304b after the correction parameters applied to the sample training data charts 2302a-2302b (e.g., to yield chart 2402) is applied to the sample training data used in charts 2304a-2304b. As shown in chart 2404, the averaged absolute forces improved by 36%, and the averaged absolute torques improved by 36%. The results in FIG. 24 show significant improvement in predicting actual sensor measurement (e.g., by accurately and reliably correcting raw measurements obtained from the sensors). Furthermore, the results show that correction parameters applied to one dataset can be applied to another dataset by changing the offset values mathematically. For example, FIG. 25 is a table showing error correction of measured forces and torques in the two training datasets (e.g., the first training dataset used in charts 2302A-2302B and 2402, and the second training dataset used in charts 2304A-2304B and 2404).

Figure 26:
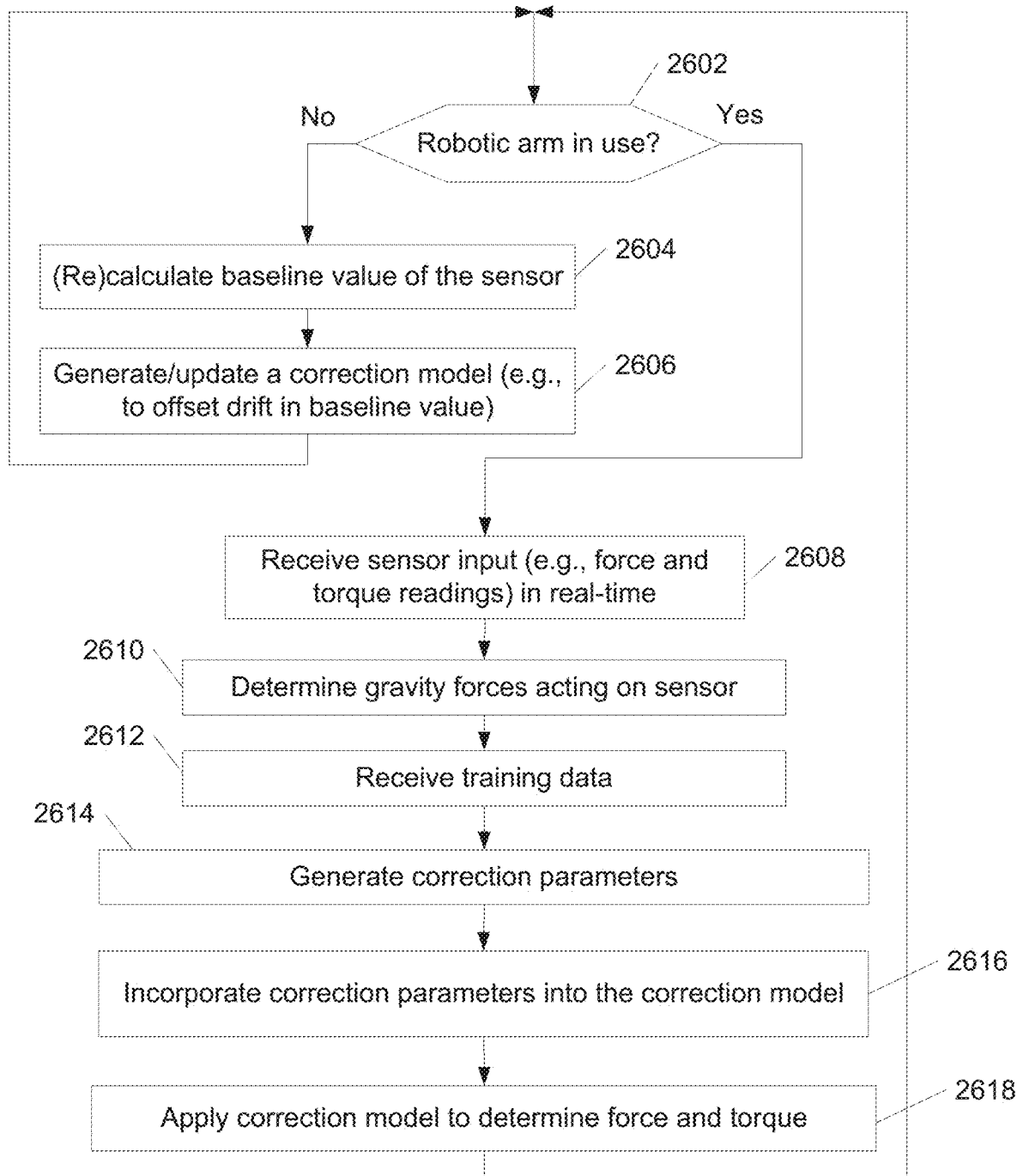
FIG. 26 is a flow chart showing an example method of calibrating and correcting a force/torque sensor associated with a collaborative robot, in accordance with a non-limiting embodiment of the present disclosure.

FIG. 26 is a flow chart showing an example method 2600 of calibrating and correcting a force/torque sensor associated with a collaborative robot, in accordance with a non-limiting embodiment of the present disclosure. The example method may be performed by a processor (e.g., processor 1102) based on computer-executable instructions stored in memory (e.g., memory 1120). In at least one embodiment, method 1120 may involve a loop where the processor may monitor whether a robotic arm is in use (block 2602). The sensor may be affixed to the robotic arm such that the sensor may move with any movement of the robotic arm. Moreover, use of the robotic arm may trigger the sensor, such that the absence of use of the robotic arm (e.g., no movement of the robotic arm) may indicate that the sensor is not in use or registering any active force or torque readings. Also or alternatively, the processor may monitor whether the sensor is active or in use.

If the robotic arm is not in use (e.g., the sensor only reads steady data under gravity effect), the processor may calculate, determine, and/or identify a baseline value of the sensor (block 2604). Since blocks 2604 may be a part of an iterative process (e.g., whenever the robotic arm or sensor is turned on or off), the baseline value may be re-calculated, determined again, or identified again at block 2604 depending on the iteration. Afterwards, the processor may generate and/or update a correction model based on the baseline value (block 2606). As discussed previously, in relation to FIG. 21, calculating baseline values when the robotic arm or sensor is not in use, and generating and/or updating a correction model based on the baseline value (e.g., "zeroing" the sensor) helps to prevent or alleviate "drifting" of baseline values.

When the robotic arm is in use, and/or when the sensor is active, the processor may receive sensor input in real-time (block 2608). For example, the processor may receive force and/or torque measurements based on forces applied at a location associated with the sensor. If the location is off center from the origin of the sensor (e.g., at a moment arm), the sensor may identify and send a measured torque value. In some embodiments, while the processor may receive sensor input in real-time (e.g., based on the sensor actively receiving data under the gravity effect), the processor may delay using such sensor input until receiving user input (e.g., after the user presses a button on the camera and/or applies a force).

The processor may determine gravity forces acting on the sensor (block 2610). For example, as discussed previously in relation to FIG. 20, forces and torques measured by the sensor under gravity effect, may need to be transformed into forces and torques under the sensor coordinate frame $F_g$ and $T_g$, respectively. Thus, determining the gravity force acting on the sensor (e.g., its direction and/or coordinate frame) may facilitate the transformation.

The processor may receive training data (block 2612) to be used for the generation of correction parameters (block 2614). As previously described, FIG. 23 shows an example of training datasets (e.g., inputs comprising sensor readings and outputs comprising the forces and torques under the gravity effect calculated based on the end-effector mass and center of mass). The correction parameters may be generated based on equations (15), (16), (7), and (8), as previously described.

The processor may then incorporate the correction parameters into the correction model (block 2616). For example, as previously described, once parameters are determined, the parameters can be substituted into equations (10-12) to solve for equations (9), (3) and (13-14).

The processor may then apply the correction model to generate a sensor correction of the sensor input (block 2618). For example, the processor may apply the correction model to the received force and/or torque values to determine the actual or corrected force and/or torque values.

CONCLUSION

It will be appreciated that each of the systems, structures, methods and procedures described herein may be implemented using one or more computer programs or components. These programs and components may be provided as a series of computer instructions on any conventional computer-readable medium, including random access memory ("RAM"), read only memory ("ROM"), flash memory, magnetic or optical disks, optical memory, or other storage media, and combinations and derivatives thereof. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Moreover, consistent with current U.S. law, it should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

What is claimed is:

1. A system for calibrating and correcting sensors associated with a collaborative robot, the system comprising:
   a robotic arm,
   a sensor affixed to a location on the robotic arm, wherein the sensor measures force and torque across six degrees of freedom (6DOF),
   a processor, and
   memory storing computer-executable instructions that, when executed by the processor, cause the processor to:
      receive, from the sensor, sensor input in real-time, the sensor input indicating a measured force applied at the location of the sensor; and
      generate, in real-time, sensor corrections to the sensor input,
         wherein the sensor corrections correspond to offset, linear, and non-linear deviations of the measured force in each sensor axis,
         wherein the sensor corrections correspond to offset, linear, and non-linear cross-coupling of the measured force between two or more sensor axes, and
         wherein the sensor corrections are determined by applying offset, linear, and non nonlinear corrections to each degree of freedom from every other degree of freedom.

2. The system of claim 1, wherein the instructions, when executed by the processor, cause the processor to:
   determine, based on the sensor corrections, a proposed movement for the robotic arm; and
   execute the proposed movement for the robotic arm.

3. The system of claim 1, wherein the instructions, when executed by the processor, cause the procedder to:
   generate, based on a mass of a payload associated with the sensor and a motion of the robotic arm, one or more calibration coefficients for the sensor, wherein the sensor corrections are based on the one or more calibration coefficients.

4. The system of claim 3, wherein the instructions, when executed by the processor, cause the processor to:
   receive, from the sensor, a measurement of a gravitational force applied at the location of the sensor, wherein the sensor corrections are further based on the gravitational force.

5. The system of claim 1, wherein the robotic arm comprises:
   a first end,
   a second end, and
   a joint connecting the first end to the second end,
      wherein the joint comprises a motor configured to rotate the joint around an axis and the sensor, wherein the sensor is configured to transmit an indication of a potential position of the joint.

6. The system of claim 5, wherein the instructions, when executed by the processor, cause the processor to:
   receive the indication of the potential position of the joint, the indication based on a translational force or a rotational force;
   apply the sensor corrections to the indication of the potential position of the joint to determine an actual position of the joint; and
   determine a movement sequence for the robotic arm based on the actual position of the joint.

7. The system of claim 6, wherein the instructions, when executed by the processor, cause the processor to:
   cause the joint of the robotic arm to rotate based on the determined movement sequence via one or more motor control signals provided to the joint,
   wherein the rotation of the joint provides power-assisted movement of the robotic arm based on the translational force or the rotational force imparted on a stereoscopic camera by an operator.

8. The system of claim 7, wherein:
   the stereoscopic camera is connected to the robotic arm, the stereoscopic camera configured to generate image data of a target surgical site.

9. The system of claim 8, wherein the stereoscopic camera includes at least one control unit having a button to enable the power-assisted movement, and
   wherein the processor is configured to:
   receive an input message indicative that the button was selected; and
   determine the movement sequence by applying the sensor corrections to the sensor input from the sensor after receiving the input message related to the button.

10. The system of claim 1, wherein the instructions, when executed by the processor, cause the processor to:
    identify a moment arm associated with the received sensor input; and
    determine, based on the moment arm and the measured force, a measured torque associated with the sensor input.

11. A system comprising:
    a robotic arm;
    a sensor affixed to a location on the robotic arm, wherein the sensor measures force and torque across six degrees of freedom (6DOF);
    a processor; and
    a memory storing computer-executable instructions that, when executed by the processor, cause the processor to:
       determine, when the robotic arm is not in use, a baseline value for the sensor;
       generate, based on the baseline value of the sensor, a correction model based on the baseline value of the sensor;

receive, in real-time when the robotic arm is in use, a sensor input from the sensor indicating a measured force;

generate, based on training data associated with the sensor, correction parameters for the correction model; and apply, in real-time, the correction model to the sensor input to generate a sensor correction for the sensor input.

12. The system of claim 11, wherein the instructions, when executed by the processor, further cause the processor to:

receive a measurement of a gravitational force applied at the location associated with the sensor input, wherein the correction parameters are further based on the gravitational force.

13. The system of claim 11, wherein the robotic arm comprises:

a first end, a second end, and a joint connecting the first end to the second end, wherein the joint comprises a motor configured to rotate the joint around an axis and the sensor, wherein the sensor is configured to transmit an indication of a potential position of the joint.

14. The system of claim 13, wherein the instructions, when executed by the processor, cause the processor to:

receive the indication of the potential position of the joint, the indication based on a translational force or a rotational force;

apply the sensor correction to the indication of the potential position of the joint to determine an actual position of the joint; and determine a movement sequence for the robotic arm based on the actual position of the joint.

15. The system of claim 14, wherein the instructions, when executed by the processor, cause the processor to:

cause the joint of the robotic arm to rotate based on the determined movement sequence via one or more motor control signals provided to the joint, wherein the rotation of one joint provides power-assisted movement of the robotic arm based on the translational force or the rotational force imparted on a stereoscopic camera by an operator.

16. The system of claim 15, wherein: the stereoscopic camera is connected to the robotic arm, the stereoscopic camera configured to generate image data of a target surgical site.

17. The system of claim 16, wherein the stereoscopic camera includes at least one control unit having a button to enable the power-assisted movement, and wherein the processor is configured to:

receive an input message indicative that the button was selected; and determine the movement sequence by applying the correction model to the sensor input from the sensor after receiving the input message related to the button.

18. The system of claim 11, wherein the instructions, when executed by the processor, cause the processor to:

identify a moment arm associated with the received sensor input; and determine, based on the moment arm and the measured force, a measured torque associated with the sensor input.

19. A method for correcting a sensor associated with a robotic arm in real-time, the method comprising:

determining, by a computing device having one or more processors, while the robotic arm is not in use, a baseline value for the sensor;

generating, based on the baseline value of the sensor, a correction model based on the baseline value of the sensor;

receiving, in real-time when the robotic arm is in use, a sensor input from the sensor indicating a measured force;

generating, based on training data associated with the sensor, correction parameters for the correction model; and applying, in real-time, the correction model to the sensor input to generate a sensor correction for the sensor input.

20. The method of claim 19, further comprising:

identifying a moment arm associated with the received sensor input; and determining, based on the moment arm and the measured force, a measured torque associated with the sensor input.

* * * * *